United States Patent
Goodacre et al.

(10) Patent No.: US 7,279,580 B2
(45) Date of Patent: Oct. 9, 2007

(54) IMIDAZO-PYRIDINE DERIVATIVES AS LIGANDS FOR GABA RECEPTORS

(75) Inventors: Simon Charles Goodacre, Benington (GB); David James Hallett, Watford (GB); Alexander Charles Humphries, Stevenage (GB); Philip Jones, Pomezia (IT); Sarah Margaret Kelly, Harlow (GB); Kevin John Merchant, Ware (GB); Kevin William Moore, Buntingford (GB); Michael Reader, Bishops Stortford (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 384 days.

(21) Appl. No.: 10/512,984

(22) PCT Filed: May 23, 2003

(86) PCT No.: PCT/GB03/02236

§ 371 (c)(1),
(2), (4) Date: Oct. 27, 2004

(87) PCT Pub. No.: WO03/099816

PCT Pub. Date: Dec. 4, 2003

(65) Prior Publication Data

US 2005/0165048 A1    Jul. 28, 2005

(30) Foreign Application Priority Data

May 24, 2002 (GB) .................... 0212048.3

(51) Int. Cl.
*C07D 471/02* (2006.01)
*C07D 491/02* (2006.01)
*C07D 498/02* (2006.01)
*A01N 43/42* (2006.01)
*A61K 31/44* (2006.01)

(52) U.S. Cl. ..................................... 546/121; 514/300
(58) Field of Classification Search ................ 546/121; 514/300
See application file for complete search history.

(56) References Cited

FOREIGN PATENT DOCUMENTS

| EP | 0563001 | 9/1993 |
|---|---|---|
| WO | WO 0078728 | 12/2000 |
| WO | WO 0138326 | 5/2001 |
| WO | WO 0190108 | 11/2001 |
| WO | WO 0238568 | 5/2002 |

OTHER PUBLICATIONS

Bordi et al., "Group I metabotropic glutamate receptors: implications for brain diseases", Progress in Neurobiology, 1999, vol. 59, pp. 55-79.*
Hand et al., "Imidazo[1,2-a] pyridine 1-Oxide. Synthesis and chemistry of a novel type of N-oxide", Journal of Organic Chemistry, 1978, vol. 43, pp. 658-663.*

* cited by examiner

*Primary Examiner*—Margaret D. Seaman
*Assistant Examiner*—Niloofar Rahmani
(74) *Attorney, Agent, or Firm*—J. Eric Thies; William Krovatin

(57) ABSTRACT

A class of 8-fluoro-3-phenylimidazo[1,2-α]pyridine derivatives, substituted at the meta position of the phenyl ring by an optionally substituted aryl or heteroaryl group, or by a pyrrolidinonyl group, which is directly attached or bridged by an oxygen atom or by a —NH— or —OCH$_2$— linkage, being selective ligands for GABA$_A$ receptors, in particular having high affinity for the α2 and/or α3 and/or α5 subunit thereof, are accordingly of benefit in the treatment and/or prevention of adverse conditions of the central nervous system, including anxiety, convulsions and cognitive disorders.

8 Claims, No Drawings

IMIDAZO-PYRIDINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB03/02236, filed May 23, 2003, which claims priority under 35 U.S.C. § 119 from GB Application No. 0212048.3, filed May 24, 2002.

The present invention relates to a class of substituted imidazopyridine derivatives and to their use in therapy. More particularly, this invention is concerned with 8-fluoroimidazo[1,2-α]pyridine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3 γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2γγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

WO 01/38326 describes a class of 3-phenylimidazo[1,2-α]pyridine derivatives which are stated to be selective ligands for GABA$_A$ receptors, in particular having high affinity for the α2 and/or α3 subunit thereof, and accordingly to be of benefit in the treatment and/or prevention of neurological disorders, including anxiety and convulsions. However, there is no disclosure nor any suggestion in that publication of substitution with a fluorine atom at the 8-position of the imidazo[1,2-α]pyridine nucleus.

The present invention provides a class of imidazo-pyridine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity (K$_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

Moreover, the compounds according to the present invention possess remarkable receptor occupancy at low doses, and interesting pharmacokinetic properties, notably in terms of improved oral bioavailability and enhanced metabolic stability.

The present invention provides a compound of formula I, or a salt or prodrug thereof:

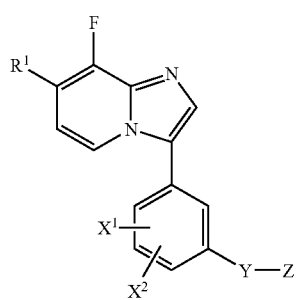

(I)

wherein
X$^1$ represents hydrogen, halogen, C$_{1-6}$ alkyl, trifluoromethyl or C$_{1-6}$ alkoxy;
X$^2$ represents hydrogen or halogen;
Y represents a chemical bond, an oxygen atom, or a —NH— or —OCH$_2$— linkage;
Z represents an optionally substituted aryl or heteroaryl group, or a pyrrolidinonyl group;
R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and
R$^a$ and R$^b$ independently represent hydrogen, hydrocarbon or a heterocyclic group.

The present invention also provides a compound of formula I as depicted above, or a salt or prodrug thereof, wherein
Y represents a chemical bond, an oxygen atom, or a —NH— linkage;
Z represents an optionally substituted aryl or heteroaryl group; and
X$^1$, X$^2$ and R$^1$ are as defined above.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted.

Illustrative substituents on the group Z include halogen, cyano, nitro, C$_{1-6}$ alkyl, trifluoromethyl, C$_{2-6}$ alkenyl, phenyl, hydroxy, C$_{1-6}$ alkoxy, trifluoromethoxy, oxy, methylenedioxy, C$_{1-6}$ alkylsulphonyl, amino, di(C$_{1-6}$)alkylamino, pyrazolyl, aminocarbonyl, formyl, C$_{2-6}$ alkoxycarbonyl and —CR$^a$=NOR$^b$, wherein R$^a$ and R$^b$ are as defined above.

Representative substituents on the group Z include halogen, cyano, C$_{1-6}$ alkyl, trifluoromethyl, C$_{2-6}$ alkenyl, phenyl, C$_{1-6}$ alkoxy, trifluoromethoxy, methylenedioxy, C$_{1-6}$ alkylsulphonyl, di(C$_{1-6}$)alkylamino, pyrazolyl, formyl and C$_{2-6}$ alkoxycarbonyl.

Typical substituents on the group Z include halogen, cyano, nitro, C$_{1-6}$ alkyl, hydroxy, C$_{1-6}$ alkoxy, oxy, C$_{1-6}$ alkylsulphonyl, amino, aminocarbonyl, formyl, C$_{2-6}$ alkoxycarbonyl and —CR$^a$=NOR$^b$, wherein R$^a$ and R$^b$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$cycloalkyl($C_{1-6}$)alkyl, indanyl, aryl and aryl ($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl $C_{1-6}$aminoalkyl, trifluoromethyl, hydroxy, $C_{1-6}$ alkoxy, aryloxy, keto, $C_{1-3}$ alkylenedioxy, nitro, cyano, carboxy, $C_{2-6}$alkoxycarbonyl, $C_{2-6}$ alkoxycarbonyl($C_{1-6}$)alkyl, $C_{2-6}$ alkylcarbonyloxy, arylcarbonyloxy, arninocarbonyloxy, $C_{2-6}$ alkylcarbonyl, arylcarbonyl, $C_{1-6}$alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the $X^1$ substituent include hydrogen, fluoro, chloro, methyl, trifluoromethyl and methoxy; in particular hydrogen or fluoro; and especially fluoro.

Typical values of $X^1$ include fluoro, chloro, methyl, trifluoromethyl and methoxy, especially fluoro.

Typical values of $X^2$ include hydrogen and fluoro, especially hydrogen.

In a preferred embodiment, Y represents a chemical bond.

In an alternative embodiment, Y represents a —OCH$_2$— linkage.

In another embodiment, Y represents an oxygen atom.

In a further embodiment, Y represents a —NH— linkage.

Suitably, the substituent Z represents an optionally substituted aryl or heteroaryl group.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents. Further values of Z include quinolinyl, isoquinolinyl, benzofuryl, benzthienyl and indolyl, any of which groups may be optionally substituted by one or more substituents. Moreover, Z may represent pyrrolidinonyl.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of illustrative substituents on the group Z include fluoro, chloro, cyano, nitro, methyl, isopropyl, trifluoromethyl, vinyl, phenyl, hydroxy, methoxy, ethoxy, trifluoromethoxy, oxy, methylenedioxy, methylsulphonyl, amino, dimethylamino, pyrazolyl, aminocarbonyl, formyl, acetyl and —CH═NOH.

Examples of specific substituents on the group Z include fluoro, chloro, cyano, methyl, isopropyl, trifluoromethyl, vinyl, phenyl, methoxy, ethoxy, trifluoromethoxy, methylenedioxy, methanesulphonyl, dimethylamino, pyrazolyl, formyl and acetyl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH═NOH.

Examples of particular substituents on the group Z include fluoro and cyano.

Illustrative values of Z include difluorophenyl, chlorophenyl, dichlorophenyl, (chloro)(fluoro)phenyl, cyanophenyl, (cyano)(fluoro)phenyl, (choro) (cyano)phenyl, nitrophenyl, isopropyl-phenyl, (fluoro)(methyl)phenyl, (chloro)(methyl)phenyl, trifluoromethyl-phenyl, vinylphenyl, methoxyphenyl, (fluoro)(methoxy)phenyl, (isopropyl)(methoxy)phenyl, ethoxyphenyl, trifluoromethoxy-phenyl, methylenedioxy-phenyl, methanesulphonyl-phenyl, (fluoro)(methanesulphonyl)-phenyl, dimethylamino-phenyl, pyrazolyl-phenyl, formylphenyl, acetylphenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, methoxy-pyrimidinyl pyrazinyl, furyl, cyano-thienyl, aminocarbonyl-thienyl, formyl-thienyl, methoxycarbonyl-thienyl, thienyl-CH=NOH, phenyl-isoxazolyl, thiazolyl, isothiazolyl, pyrrolyl, pyrazolyl, imidazolyl, triazolyl, methyl-triazolyl, methyl-tetrazolyl, quinolinyl, methyl-quinolinyl, isoquinolinyl, benzofuryl, benzthienyl, indolyl and pyrrolidinonyl.

Representative values of Z include difluorophenyl, chlorophenyl, dichlorophenyl, (chloro)(fluoro)phenyl, cyanophenyl, (cyano)(fluoro)phenyl, (chloro)(cyano)phenyl, isopropyl-phenyl, (fluoro)(methyl)phenyl, (chloro)(methyl)phenyl, trifluoromethyl-phenyl, vinylphenyl, methoxyphenyl, (fluoro)(methoxy)phenyl, (isopropyl)(methoxy)phenyl, ethoxyphenyl, trifluoromethoxy-phenyl, methylenedioxy-phenyl, methanesulphonyl-phenyl, (fluoro)(methanesulphonyl)-phenyl, dimethylamino-phenyl, pyrazolyl-phenyl, formylphenyl, acetylphenyl, pyridinyl, difluoro-pyridinyl, cyano-pyridinyl, methoxy-pyridinyl, pyrimidinyl, methoxy-pyrimidinyl, furyl, phenyl-isoxazolyl, pyrrolyl, imidazolyl, methyl-triazolyl, quinolinyl, methyl-quinolinyl, isoquinolinyl, benzofuryl, benzthienyl, indolyl and pyrrolidinonyl.

Detailed values of Z include cyanophenyl, (cyano)(fluoro)phenyl, (chloro)(cyano)phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl-CH=NOH, thiazolyl, isothiazolyl, pyrrolyl, pyrazolyl, imidazolyl, triazolyl and methyl-tetrazolyl.

Specific values of Z include cyanophenyl, (cyano)(fluoro)phenyl, pyridinyl, difluoro-pyridinyl and cyano-pyridinyl.

In one embodiment, Z represents 2-cyanophenyl.

In another embodiment, Z represents 2-cyano-4-fluorophenyl.

In an additional embodiment, Z represents 2-cyano-6-fluorophenyl.

In a further embodiment, Z represents pyridin-3-yl.

In a still further embodiment, Z represents 3,5-difluoropyridin-2-yl.

In a yet further embodiment, Z represents 3-cyanopyridin-2-yl.

Typically, $R^1$ represents hydrogen, hydrocarbon, a heterocyclic group, halogen, cyano, trifluoromethyl, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$) alkyl, $C_{3-7}$cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl and —$CR^a$=$NOR^b$, in which $R^a$ and $R^b$ are as defined above.

Representative values of $R^1$ include hydrogen, halo($C_{1-6}$)alkyl, hydroxy($C_{1-6}$)alkyl, halogen and trifluoromethyl. Moreover, $R^1$ may suitably represent $C_{2-6}$ alkoxycarbonyl.

Individual values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

Particular values of $R^1$ include hydrogen, hydroxypropyl (especially 2-hydroxyprop-2-yl), fluoropropyl (especially 2-fluoroprop-2-yl), chloro, trifluoromethyl and methoxycarbonyl.

In one embodiment, $R^1$ represents hydrogen. In a favoured embodiment, $R^1$ represents 2-hydzoxyprop-2-yl. In another embodiment, $R^1$ represents 2-fluoroprop-2-yl. In an additional embodiment, $R^1$ represents trifluoromethyl. In a further embodiment, $R^1$ represents chloro. In a still further embodiment, $R^1$ represents methoxycarbonyl.

Suitably, $R^2$ is hydrogen.

Suitably, $R^3$ represents hydrogen or dimethylaminoethyl, especially hydrogen.

A particular sub-class of compounds according to the invention is represented by the compounds of formula IIA, and salts and prodrugs thereof:

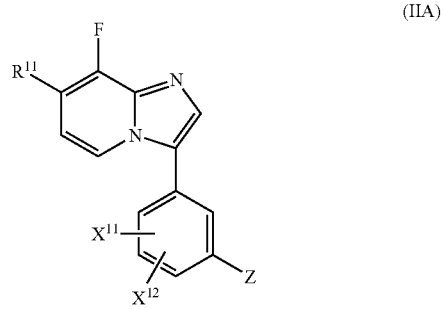

(IIA)

wherein

Z is as defined above;

$X^{11}$ represents hydrogen, fluoro, chloro, methyl, trifluoromethyl or methoxy;

$X^{12}$ represents hydrogen or fluoro;

$R^{11}$ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$akoxycarbonyl($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alxylamino($C_{1-6}$)alkyl.

Suitable values of $X^{11}$ include hydrogen and fluoro, especially fluoro.

Typical values of $X^{11}$ include fluoro, chloro, methyl, trifluoromethyl and methoxy.

A particular value of $X^{11}$ is fluoro.

In a favoured embodiment, $X^{12}$ represents hydrogen. In another embodiment, $X^{12}$ represents fluoro.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Representative values of $R^{11}$ include hydrogen, hydroxy($C_{1-6}$)alkyl, fluoro($C_{1-6}$)alkyl, halogen and trifluoromethyl. Moreover, $R^{11}$ may suitably represent $C_{2-6}$ alkoxycarbonyl.

Individual values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^2$=$NOR^3$, in which $R^2$ and $R^3$ are as defined above.

Particular values of $R^{11}$ include hydrogen, hydroxypropyl (especially 2-hydroxyprop-2-yl), fluoropropyl (especially 2-fluoroprop-2-yl), chloro, trifluoromethyl and methoxycarbonyl.

In one embodiment, $R^{11}$ represents hydrogen. In a favoured embodiment, $R^{11}$ represents 2-hydroxyprop-2-yl. In another embodiment, $R^{11}$ represents 2-fluoroprop-2-yl. In an additional embodiment, $R^{11}$ represents trifluoromethyl. In a further embodiment, $R^{11}$ represents chloro. In a still further embodiment, $R^{11}$ represents methoxycarbonyl.

One representative subset of the compounds of formula IIA above is represented by the compounds of formula IIB, and salts and prodrugs thereof:

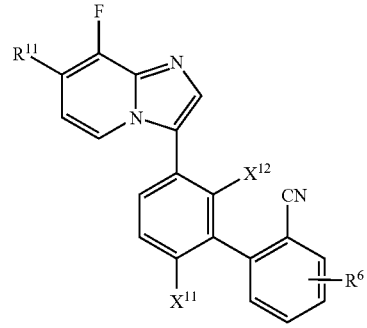

(IIB)

wherein $X^{11}$, $X^{12}$ and $R^{11}$ are as defined above; and $R^6$ represents hydrogen or fluoro.

In one embodiment, $R^6$ is hydrogen.

In another embodiment, $R^6$ is fluoro, in which case the fluorine atom $R^6$ is favourably attached to the phenyl ring at the 4-, 5- or 6-position (relative to the cyano group at position 2).

Another representative subset of the compounds of formula IIA above is represented by the compounds of formula IIC, and salts and prodrugs thereof:

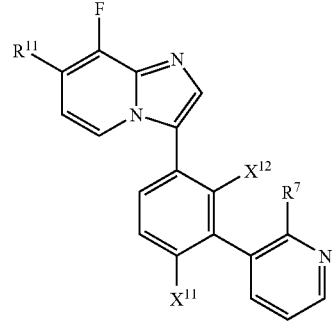

(IIC)

wherein $X^{11}$, $X^{12}$ and $R^{11}$ are as defined above; and $R^7$ represents hydrogen, fluoro, cyano or methyl.

In one embodiment, $R^7$ is hydrogen.

In an additional embodiment, $R^7$ is fluoro.

In another embodiment, $R^7$ is cyano.

In a further embodiment, $R^7$ is methyl.

A further representative subset of the compounds of formula IIA above is represented by the compounds of formula IID, and salts and prodrugs thereof:

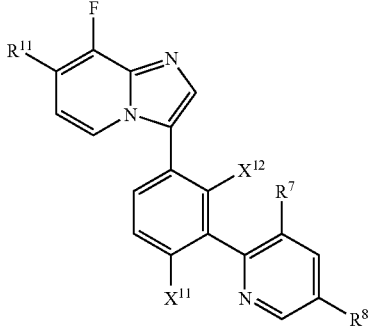

(IID)

wherein $X^{11}$, $X^{12}$, $R^7$ and $R^{11}$ are as defined above; and $R^8$ represents hydrogen or fluoro.

Suitably, $R^8$ represents hydrogen.

In another embodiment, $R^8$ represents fluoro.

Specific compounds within the scope of the present invention include:

8-fluoro-3-[3-(pyridin-3-yl)phenyl]imidazo[1,2-α]pyridine;

2-[8-fluoro-3-[4-fluoro-3-(pyridin-3-yl)phenyl]imidazo[1,2-α]pyridin-7-yl]propan-2-ol;

2'-fluoro-5'-[8-fluoro-7-(2-hydroxyprop-2-yl)imidazo[1,2-α]pyridin-3-yl]biphenyl-2-carbonitrile;

7-chloro-8-fluoro-3-[4-fluoro-3-(pyridin-3-yl)phenyl]imidazo[1,2-α]pyridine;

5'-[7-chloro-8-fluoroimidazo[1,2-α]pyridin-3-yl]-2'-fluorobiphenyl-2-carbonitrile;

4,2'-difluoro-5'-[8-fluoro-7-(1-hydroxy-1-methylethyl)imidazo[1,2-α]pyridin-3-yl]biphenyl-2-carbonitrile;

2-{3-[3-(3,5-difluoropyridin-2-yl)-4-fluorophenyl]-8-fluoroimidazo[1,2-α]pyridin-7-yl}propan-2-ol;

6,2'-difluoro-5'-[8-fluoro-7-(1-hydroxy-1-methylethylimidazo[1,2-α]pyridin-3-yl]biphenyl-2-carbonitrile;

2-{2-fluoro-5-[8-fluoro-7-(1-hydroxy-1-methylethyl)imidazo[1,2-α]pyridin-3-yl]phenyl}nicotinonitrile;

3,2'-difluoro-5'-[8-fluoro-7-(1-hydroxy-1-methylethyl)imidazo[1,2-α]pyridin-3-yl]biphenyl-2-carbonitrile;

4-fluoro-3'-[8-fluoro-7-(1-hydroxy-1-methylethyl)imidazo[1,2-α]pyridin-3-yl]biphenyl-2-carbonitrile;

4,2'-difluoro-5'-(8-fluoroimidazo[1,2-α]pyridin-3-yl)biphenyl-2-carbonitrile;

5'-(7-chloro-8-fluoroimidazo[1,2-α]pyridin-3-yl)-4,2'-difluorobiphenyl-2-carbonitrile;

3-(2'-cyano-2,4'-difluorobiphenyl-5-yl)-8-fluoroimidazo[1,2-α]pyridine-7-carboxylic acid methyl ester;

4,2'-difluoro-5'-[8-fluoro-7-(1-fluoro-1-methylethyl)imidazo[1,2-α]pyridin-3-yl]biphenyl-2-carbonitrile;

4'-fluoro-3'-[8-fluoro-7-(1-hydroxy-1-methylethyl)imidazo[1,2-α]pyridin-3-yl]biphenyl-2-carbonitrile;

3'-fluoro-5'-[8-fluoro-7-(1-hydroxy-1-methylethyl)imidazo[1,2-α]pyridin-3-yl]biphenyl-2-carbonitrile;

2-{3-[3-(3,5-difluoropyridin-4-yl)-4-fluorophenyl]-8-fluoroimidazo[1,2-α]pyridin-7-yl}propan-2-ol;

5,2'-difluoro-5'-[8-fluoro-7-(1-hydroxy-1-methylethyl)imidazo[1,2-α]pyridin-3-yl]biphenyl-2-carbonitrile;

2'-fluoro-3'-[8-fluoro-7-(1-hydroxy-1-methylethyl)imidazo[1,2-α]pyridin-3-yl]biphenyl-2-carbonitrile;

3'-[8-fluoro-7-(1-hydroxy-1-methylethyl)imidazo[1,2-α]pyridin-3-yl]-6,2',6'-trifluorobiphenyl-2-carbonitrile;

4,4'-difluoro-3'-[8-fluoro-7-(1-hydroxy-1-methylethyl)imidazo[1,2-α]pyridin-3-yl]biphenyl-2-carbonitrile;

3-chloro-2'-fluoro-5'-[8-fluoro-7-(1-hydroxy-1-methylethyl)imidazo[1,2-α]pyridin-3-yl]biphenyl-4-carbonitrile;

1-{2-fluoro-5-[8-fluoro-7-(1-hydroxy-1-methylethyl)imidazo[1,2-α]pyridin-3-yl]phenyl}pyrrolidin-2-one;

2-{8-fluoro-3-[4-fluoro-3-(imidazol-1-yl)phenyl]imidazol[1,2-α]pyridin-7-yl}-propan-2-ol;

4,3'-difluoro-5'-[8-fluoro-7-(1-hydroxy-1-methylethyl)imidazo[1,2-α]pyridin-3-yl]biphenyl-2-carbonitrile;

3'-[8-fluoro-7-(1-hydroxy-1-methylethyl)imidazo[1,2-α]pyridin-3-yl]-4,2',6'-trifluorobiphenyl-2-carbonitrile;

2-{8-fluoro-3-[4-fluoro-3-(1-methyl-1H-[1,2,3]triazol-4-ylmethoxy)phenyl]-imidazo[1,2-α]pyridin-7-yl}propan-2-ol;

3-(2,4'-difluoro-2'-methanesulfonylbiphenyl-5-yl)-8-fluoro-7-(1-hydroxy-1-methylethyl)imidazo[1,2-α]pyridine;

1-{2'-fluoro-5'-[8-fluoro-7-(1-hydroxy-1-methylethyl)imidazo[1,2-α]pyridin-3-yl]biphenyl-4-yl}ethanone;

2-[3-(2,4'-difluoro-2'-methylbiphenyl-5-yl)-8-fluoroimidazo[1,2-α]pyridin-7-yl]propan-2-ol;

2'-fluoro-5'-[8-fluoro-7-(1-hydroxy-1-methylethyl)imidazo[1,2-α]pyridin-3-yl]biphenyl-3-carbonitrile;

1-{2'-fluoro-5'-[8-fluoro-7-(1-hydroxy-1-methylethyl)imidazo[1,2-α]pyridin-3-yl]biphenyl-3-yl}ethanone;

2-[8-fluoro-3-(2-fluoro-5'-isopropyl-2'-methoxybiphenyl-5-yl)imidazo[1,2-α]pyridin-7-yl]propan-2-ol;

2'-fluoro-5'-[8-fluoro-7-(1-hydroxy-1-methylethyl)imidazo[1,2-α]pyridin-3-yl]biphenyl-4-carbaldehyde;

2-[8-fluoro-3-(2-fluoro-4'-trifluoromethylbiphenyl-5-yl)imidazo[1,2-α]pyridin-7-yl]propan-2-ol;

2'-fluoro-5'-[8-fluoro-7-(1-hydroxy-1-methylethyl)imidazo[1,2-α]pyridin-3-yl]biphenyl-4-carbonitrile;

2-[8-fluoro-3-(2,2',4'-trifuorobiphenyl-5-yl)imidazo[1,2-α]pyridin-7-yl]-propan-2-ol;

2-[8-fluoro-3-(2-fluoro-3'-trifluoromethoxybiphenyl-5-yl)imidazo[1,2-α]pyridin-7-yl]propan-2-ol;

2-[8-fluoro-3-(2-fluoro-2'-trifluoromethylbiphenyl-5-yl)imidazo[1,2-α]pyridin-7-yl]propan-2-ol;

2-[8-fluoro-3-(2-fluoro-4'-vinylbiphenyl-5-yl)imidazo[1,2-α]pyridin-7-yl]-propan-2-ol;

2-[3-(2'-ethoxy-2-fluorobiphenyl-5-yl)-8-fluoroimidazo[1,2-α]pyridin-7-yl]-propan-2-ol;

2-[8-fluoro-3-(2-fluoro-2'-trifluoromethoxybiphenyl-5-yl)imidazo[1,2-α]pyridin-7-yl]propan-2-ol;

2-[3-(2,4'-difluoro-2'-methoxybiphenyl-5-yl)-8-fluoroimidazo[1,2-α]pyridin-7-yl]propan-2-ol;

2,2'-difluoro-5'-[8-fluoro-7-(1-hydroxy-1-methylethyl)imidazo[1,2-α]pyridin-3-yl]biphenyl-4-carbonitrile;

2-[3-(4'-dimethylamino-2-fluorobiphenyl-5-yl)-8-fluoroimidazo[1,2-α]pyridin-7-yl]propan-2-ol;

2-{8-fluoro-3-[4-fluoro-3-(1H-indol-5-yl)phenyl]imidazo[1,2-α]pyridin-7-yl}-propan-2-ol;

2-[3-(2,3'-difluoro-2'-methylbiphenyl-5-yl)-8-fluoroimidazo[1,2-α]pyridin-7-yl]propan-2-ol;

2-[3-(3'-chloro-2-fluoro-2'-methylbiphenyl-5-yl)-8-fluoroimidazo[1,2-α]pyridin-7-yl]propan-2-ol;

2-{8-fluoro-3-[4-fluoro-3-(2-methoxypyrimidin-5-yl)phenyl]imidazo[1,2-α]pyridin-7-yl}propan-2-ol;

2-{8-fluoro-3-[4-fluoro-3-(pyrimidin-5-yl)phenyl]imidazo[1,2-α]pyridin-7-yl}-propan-2-ol;

2-{8-fluoro-3-[4-fluoro-3-(2-methylquiuolin-5-yl)pheny]imidazo[1,2-α]pyridin-7-yl}propan-2-ol;

2-{8-fluoro-3-[4-fluoro-3-(2-methoxypyridin-5-yl)phenyl]imidazo[1,2-α]pyridin-7-yl}propan-2-ol;

2-[3-(3'-chloro-2,4'-difluorobiphenyl-5-yl)-8-fluoroimidazo[1,2-α]pyridin-7-yl]propan-2-ol;

2-[3-(3'-chloro-2-fluorobiphenyl-5-yl)-8-fluoroimidazo[1,2-α]pyridin-7-yl]-propan-2-ol;

2-[3-(2',4'-dichloro-2-fluorobiphenyl-5-yl)-8-fluoroimidazo[1,2-α]pyridin-7-yl]propan-2-ol;

2-[3-(3',5'-dichloro-2-fluorobiphenyl-5-yl)-8-fluoroimidazo[1,2-α]pyridin-7-yl]propan-2-ol;

2-[3-(3',4'-dichloro-2-fluorobiphenyl-5-yl)-8-fluoroimidazo[1,2-α]pyridin-7-yl]propan-2-ol;

2-[8-fluoro-3-(2-fluoro-4'-methanesulfonylbiphenyl-5-yl)imidazo[1,2-α]pyridin-7-yl]propan-2-ol;

2-[3-(2',3'-dichloro-2-fluorobiphenyl-5-yl)-8-fluoroimidazo[1,2-α]pyridin-7-yl]propan-2-ol;

2-{3-[3-(benzo[b]thien-7-yl)-4-fluorophenyl]-8-fluoroimidazo[1,2-α]pyridin-7-yl}propan-2-ol;

2-{8-fluoro-3-[2-fluoro-2'-(pyrazol-1-yl)biphenyl-5-yl)imidazo[1,2-α]pyridin-7-yl}propan-2-ol;

2-{8-fluoro-3-[4-fluoro-3-(3-phenylisoxazol-5-yl)phenyl]imidazo[1,2-α]pyridin-7-yl}propan-2-ol;

2-{8-fluoro-3-[4-fluoro-3-(isoquinolin-5-yl)phenyl]imidazo[1,2-α]pyridin-7-yl}propan-2-ol;

2-[8-fluoro-3-(2,3',5'-trifluorobiphenyl-5-yl)imidazo[1,2-α]pyridin-7-yl]propan-2-ol;

2-[8-fluoro-3-(2-fluoro-3'-isopropylbiphenyl-5-y)imidazo[1,2-α]pyridin-7-yl]propan-2-ol;

2-[8-fluoro-3-(2, 3',4'-trifluorobiphenyl-5-yl)imidazo[1,2-α]pyridin-7-yl]-propan-2-ol;

2-{8-fluoro-3-[4-fluoro-3-(quinolin-5-yl)phenyl]imidazo[1,2-α]pyridin-7-yl}propan-2-ol;

2-[3-(3'-chloro-2,2'-difluorobiphenyl-5-yl)-8-fluoroimidazo[1,2-α]pyridin-7-yl]propan-2-ol;

2-[3-(5'-chloro-2,2'-difluorobiphenyl-5-yl)-8-fluoroimidazo[1,2-α]pyridin-7-yl]propan-2-ol;

4,2'-difluoro-5'-[8-fluoro-7-(1-hydroxy-1-methylethyl)imidazo[1,2-α]pyridin-3-yl]biphenyl-3-carbonitrile;

2-{8-fluoro-3-[4-fluoro-3-(fur-2-yl)phenyl]imidazo[1,2-α]pyridin-7-yl}-propan-2-ol;

2-{3-[3-(benzo[1,3]dioxol-5-yl)-4-fluorophenyl]-8-fluoroimidazo[1,2-α]pyridin-7-yl}propan-2-ol;

2-[8-fluoro-3-(2-fluoro-3'-trifluoromethylbiphenyl-5-yl)imidazo[1,2-α]pyridin-7-yl]propan-2-ol;

2-{8-fluoro-3-[4-fluoro-3-(1H-pyrrol-2-yl)phenyl]imidazo[1,2-α]pyridin-7-yl}propan-2-ol;

2-{3-[3-(benzofur-2-yl)-4-fluorophenyl]-8-fluoroimidazo[1,2-α]pyridin-7-yl}propan-2-ol;

2-[3-(2,2'-difluoro-4'-methoxybiphenyl-5-yl)-8-fluoroimidazo[1,2-α]pyridin-7-yl]propan-2-ol;

2-[8-fluoro-3-(2-fluoro-2'-methoxybiphenyl-5-yl)imidazo[1,2-α]pyridin-7-yl]propan-2-ol;

4,2'-difluoro-5'-(8-fluoro-7-trifluoromethylimidazo[1,2-α]pyridin-3-yl)-biphenyl-2-carbonitrile;

6,2'-difluoro-5'-(8-fluoro-7-trifluoromethylimidazo[1,2-α]pyridin-3-yl)-biphenyl-2-carbonitrile;

3-[3-(3,5-difluoropyridin-2-yl)-4-fluorophenyl]-8-fluoro-7-trifluoromethyl-imidazo[1,2-α]pyridine;

2-[2-fluoro-5-(8-fluoro-7-trifluoromethylimidazo[1,2-α]pyridin-3-yl)-phenyl]nicotinonitrile;

1-[2-fluoro-5-(8-fluoro-7-trifluoromethylimidazo[1,2-α]pyridin-3-yl)-phenyl]pyrrolidin-2-one;

3-(2,4'-difluoro-2'-methanesulfonylbiphenyl-5-yl)-8-fluoro-7-trifluoromethylimidazo[1,2-α]pyridine;

2-{8-fluoro-3-[4-fluoro-3-(2-methyl-2H-[1,2,4]triazol-3-ylmethoxy)phenyl]-imidazo[1,2-α]pyridin-7-yl}propan-2-ol;

8-fluoro-3-[4-fluoro-3-(1-methyl-1H-[1,2,3]triazol-4-ylmethoxy)phenyl]-7-trifluoromethylimidazo[1,2-α]pyridine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670-678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109-117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206-213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492-501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101-108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action.

For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

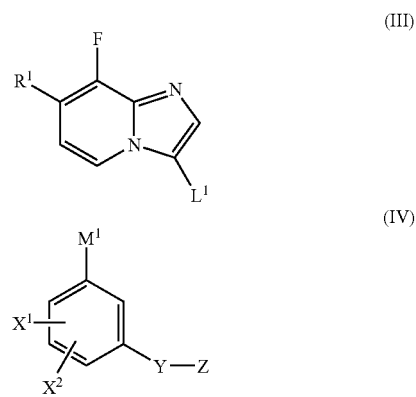

wherein $X^1$, $X^2$, Y, Z and $R^1$ are as defined above, $L^1$ represents a suitable leaving group, and Ml represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis(triphenylphosphine)-palladium(0). The reaction is conveniently carried out at an elevated temperature in a solvent such as N,N-dimethylacetamide, 1,4-dioxane or tetrahydrofuran, advantageously in the presence of potassium phosphate, copper(I) iodide, sodium carbonate or cesium carbonate. Alternatively, the transition metal catalyst employed may be dichloro[1,1'-bis(diphenylphosphino)ferrocene]palladium (II), in which case the reaction is conveniently effected at an elevated temperature in a solvent such as N,N-dimethylformamide, advantageously in the presence of potassium phosphate.

In an alternative procedure, the compounds according to the present invention may be prepared by a process which comprises reacting a compound of formula V with a compound of formula VI:

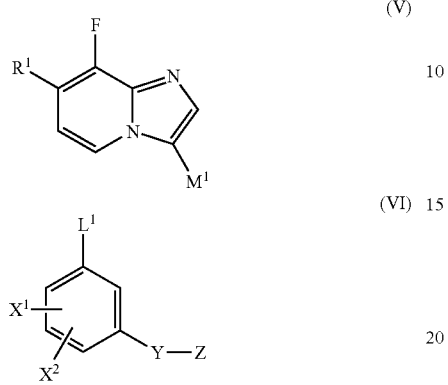

(V)

(VI)

wherein $X^1$, $X^2$, Y, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents a chemical bond may be prepared by a process which comprises reacting a compound of formula VII with a compound of formula VIII:

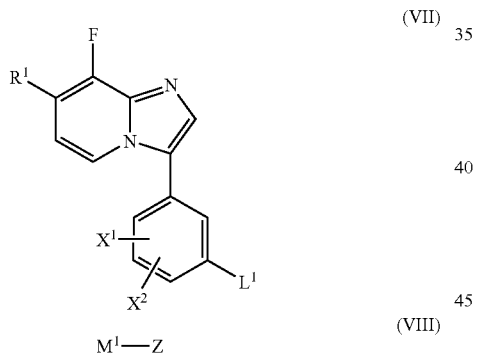

(VII)

(VIII)

wherein $X^1$, $X^2$, Z, $R^1$, $L^1$ and $M^1$ are as defined above; in the presence of a transition metal catalyst; under conditions analogous to those described above for the reaction between compounds III and IV.

In the compounds of formula VI and VII above, the leaving group $L^1$ is typically trifluoromethanesulfonyloxy (triflyloxy); or a halogen atom, e.g. bromo or chloro.

The transition metal catalyst of use in the reaction between compounds VII and VIII above may suitably be tris(dibenzylideneacetone)-dipalladium(0), in which case the reaction is conveniently effected at an elevated temperature in a solvent such as aqueous 1,4-dioxane, typically in the presence of tri-tert-butylphosphine and potassium phosphate.

Alternatively, the compounds according to the present invention in which Y represents a chemical bond may be prepared by a process which comprises reacting a compound of formula IX with a compound of formula X:

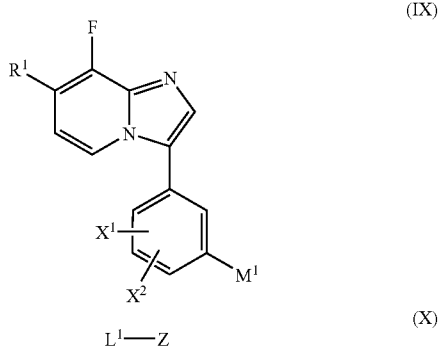

(IX)

(X)

wherein $X^1$, $X^2$, Z, $R^1$, $L^1$ and $M^1$ are as defined above; in the presence of a transition metal catalyst; under conditions analogous to those described above for the reaction between compounds III and IV.

In an additional procedure, the compounds according to the present invention in which Y represents an oxygen atom may be prepared by a process which comprises reacting a compound of formula X as defined above with a compound of formula XI:

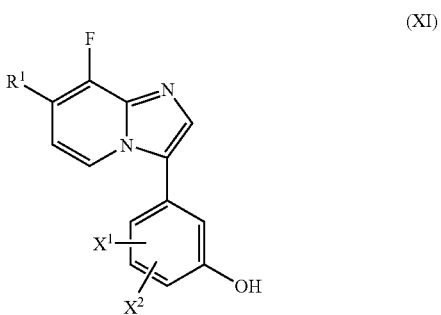

(XI)

wherein $X^1$, $X^2$ and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

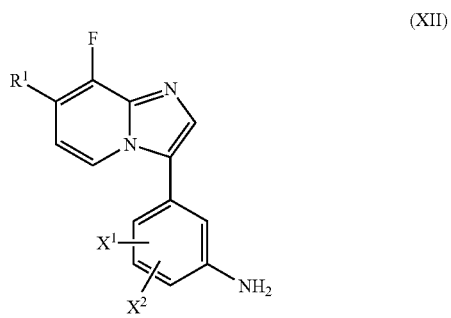

(XII)

wherein $X^1$, $X^2$ and $R^1$ are as defined above.

In relation to the reaction between compounds X and XII, the leaving group L¹ in the compounds of formula X may suitably represent fluoro.

The reaction between compounds X and XII is conveniently carried out by heating the reactants, typically at a temperature in the region of 120° C., in a solvent such as N,N-dimethylformamide.

Where M¹ in the intermediates of formula IV and IX above represents a boronic acid moiety —B(OH)₂ or a cyclic ester thereof formed with pinacol or neopentyl glycol, the relevant compound IV or IX may be prepared by reacting bis(pinacolato)diboron or bis(neopentyl glycolato)diborane respectively with a compound of formula VI or VII as defined above; in the presence of a transition metal catalyst.

The transition metal catalyst of use in the reaction between bis(pinacolato)diboron or bis(neopentyl glycolato) diborane and compound VI or VII is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where L¹ in the intermediates of formula VII above represents triflyloxy, the relevant compound VII may be prepared by reacting the appropriate compound of formula XI as defined above with triflic anhydride, typically in the presence of pyridine. Analogous conditions may be utilised for preparing a compound of formula VI wherein L¹ represents triflyloxy from the corresponding hydroxy precursor.

The intermediates of formula XI above may suitably be prepared from the appropriate methoxy-substituted precursor of formula XIII:

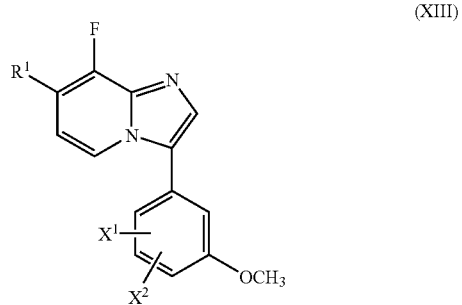

(XIII)

wherein X¹, X² and R¹ are as defined above; by treatment with boron tribromide, typically in chloroform or dichloromethane; or with hydrogen bromide, typically in acetic acid at reflux.

The intermediates of formula XII and XIII above may be prepared by reacting a compound of formula III as defined above with the appropriate compound of formula XIV:

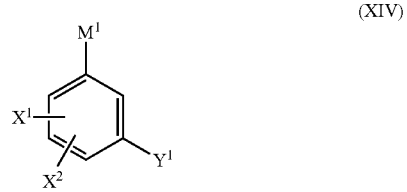

(XIV)

wherein X¹, X² and M¹ are as defined above, and Y¹ represents amino or methoxy; in the presence of a transition metal catalyst; under conditions analogous to those described above for the reaction between compounds III and IV. In particular, the transition metal catalyst of use in the reaction between compounds III and XIV is suitably tetrakis (triphenylphosphine)-palladium(0), in which case the reaction is conveniently carried out at an elevated temperature in a solvent such as aqueous 1,2-dimethoxyethane, advantageously in the presence of sodium carbonate.

Where M¹ in the intermediates of formula V above represents —Sn(Alk)₃ and Alk is as defined above, this compound may be prepared by reacting a compound of formula III as defined above with a reagent of formula (Alk)₃Sn-Hal, in which Hal represents a halogen atom, typically chloro. The reaction is conveniently effected by treating compound III with isopropylmagnesium chloride, typically in a solvent such as tetrahydrofuran, with subsequent addition of the stannyl reagent (Alk)₃Sn-Hal.

Where L¹ in the intermediates of formula III above represents bromo, this compound may be prepared by bromination of the corresponding compound of formula XV:

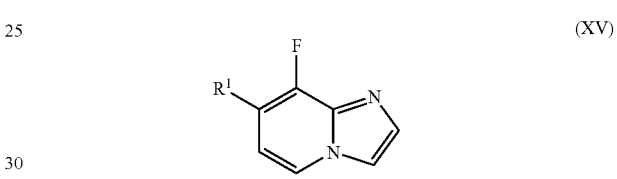

(XV)

wherein R¹ is as defined above; typically by treatment with bromine in methanol, in the presence of sodium acetate and optionally also potassium bromide.

The intermediates of formula XV may be prepared by reacting chloroacetaldehyde or bromoacetaldehyde, or an acetal derivative thereof, e.g. the dimethyl or diethyl acetal thereof, with the requisite compound of formula XVI:

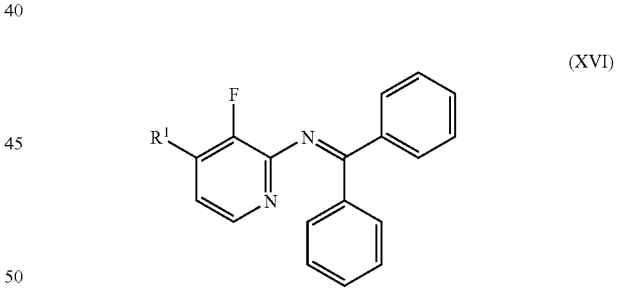

(XVI)

wherein R¹ is as defined above.

Where chloroacetaldehyde or bromoacetaldehyde is utilised as one of the reactants, the reaction is conveniently carried out by heating the reactants under basic conditions in a suitable solvent, e.g. sodium methoxide or sodium hydrogencarbonate in a lower alkanol such as methanol, ethanol or isopropanol. Where an acetal derivative of chloroacetaldehyde or bromoacetaldehyde, e.g. the dimethyl or diethyl acetal thereof, is utilised as one of the reactants, the reaction is conveniently effected by heating the reactants under acidic conditions, e.g. in aqueous hydrobromic acid.

In a still further procedure, the compounds according to the present invention may be prepared by a process which comprises reacting a compound of formula XVI as defined above with a compound of formula XVII:

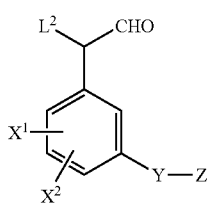

(XVII)

wherein $X^1$, $X^2$, Y and Z are as defined above, and $L^2$ represents a suitable leaving group; under conditions analogous to those described above for the reaction between chloroacetaldehyde or bromoacetaldehyde, or an acetal derivative thereof, and compound XVI.

The leaving group $L^2$ is suitably a halogen atom, e.g. bromo.

The intermediates of formula XVI may be prepared by reacting benzophenone imine with a compound of formula XVIII:

(XVIII)

wherein $R^1$ is as defined above.

The reaction is conveniently accomplished by heating in a solvent such as toluene, advantageously in the presence of a base such as cesium carbonate or sodium tert-butoxide, a transition metal catalyst such as palladium(II) acetate or tris(dibenzylideneacetone)dipalladium(0), and 2,2'-bis(diphenylphosphino)-1,1'-binaphthyl (BINAP).

In a yet further procedure, the compounds according to the present invention wherein $R^1$ represents an aryl or heteroaryl moiety may be prepared by a process which comprises reacting a compound of formula XIX with a compound of formula XX:

$$R^{1a}-M^1$$ (XIX)

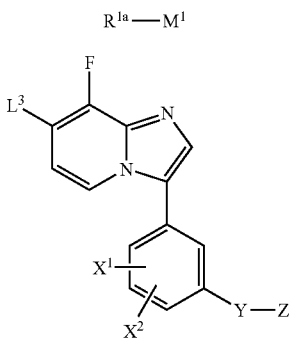

(XX)

wherein $X^1$, $X^2$, Y, Z and $M^1$ are as defined above, $R^{1a}$ represents an aryl or heteroaryl moiety, and $L^3$ represents a suitable leaving group; in the presence of a transition metal catalyst.

The leaving group $L^3$ is typically a halogen atom, e.g. chloro.

The transition metal catalyst of use in the reaction between compounds XIX and XX is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)dipalladium(0), in which case the reaction is conveniently effected at an elevated temperature in a solvent such as 1,4-dioxane, typically in the presence of tri-tert-butylphosphine and cesium carbonate.

Where $L^3$ in the compounds of formula XX above represents a halogen atom, these compounds correspond to compounds of formula I as defined above wherein $R^1$ represents halogen, and they may therefore be prepared by any of the methods described above for the preparation of the compounds according to the invention.

The compounds according to the invention in which Y represents a chemical bond and Z represents pyrrol-1-yl may be prepared by reacting a compound of formula XII as defined above with 2,5-dimethoxytetrahydrofuran. The reaction is conveniently accomplished at an elevated temperature in a solvent such as acetic acid.

Furthermore, the compounds according to the invention may be prepared by a process which comprises reacting a compound of formula VI as defined above with a compound of formula XV as defined above in the presence of a transition metal catalyst.

The transition metal catalyst of use in the reaction between compounds VI and XV is suitably tetrakis(triphenylphosphine)-palladium(0), in which case the reaction is conveniently effected at an elevated temperature in a solvent such as 1,4dioxane, typically in the presence of cesium carbonate.

Where they are not commercially available, the starting materials of formula VI, VIII, X, XIV, XVII, XVIII and XIX may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents $-C(O-Alk^1)_2R^a$ initially obtained, wherein $Alk^1$ is $C_{1-6}$ alkyl, typically methyl or ethyl, may be converted into the corresponding compound of formula I wherein $R^1$ represents $-COR^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents $C_{2-6}$ alkoxycarbonyl may be reduced with lithium aluminium hydride to the corresponding compound of formula I wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula $H_2N-OR^b$ to provide a compound of formula I wherein $R^1$ represents $-CH=NOR^b$. Furthermore, a compound of formula I wherein $R^1$ represents $-CH=NOH$ may be treated with triethylamine in the presence of 1,1'-carbonyldiimidazole to afford a corresponding compound of formula I wherein $R^1$ represents cyano. Alternatively, the compound of formula I wherein R$^1$ represents formyl may be reacted with a Grignard reagent of formula R$^a$MgBr to afford a compound of formula I wherein R$^1$ represents —CH(OH)R$^a$, and this compound may in turn be oxidised using manganese dioxide to the corresponding compound of formula I wherein R$^1$ represents —COR$^a$. The latter compound may then be condensed with a hydroxylamine derivative of formula H$_2$N—OR$^b$ to provide a compound of formula I wherein R$^1$ represents —CR$^a$=NOR$^b$. A compound of formula I wherein R$^1$ represents —CH(OH)R$^a$ may be converted into the corresponding compound of formula I wherein R$^1$ represents —CGHFR$^a$ by treatment with (diethylamino)sulfur trifluoride (DAST). Similarly, a compound of formula I wherein R$^1$ represents —COR$^a$ may be converted into the corresponding compound of formula I wherein R$^1$ represents —CF$_2$R$^a$ by treatment with DAST. A compound of formula I wherein R$^1$ represents 2-hydroxyprop-2-yl may be converted into the corresponding compound wherein R$^1$ represents 2-fluoroprop-2-yl by treatment with HF/pyridine. A compound of formula I wherein R$^1$ represents amino may be converted into the corresponding compound of formula I wherein R$^1$ represents chloro by diazotisation, using sodium nitrite, followed by treatment with copper(I) chloride. A compound of formula I wherein R$^1$ represents —COCH$_3$ may be treated with thioacetamide in the presence of pyridinium tribromide to furnish the corresponding compound of formula I wherein R$^1$ represents 2-methylthiazol-5-yl. Moreover, a compound of formula I wherein R$^1$ is formyl may be treated with p-tolylsulfonyl)methyl isocyanide (TosMIC) in the presence of potassium carbonate to afford the corresponding compound of formula I wherein R$^1$ represents oxazol-5-yl. A compound of formula I wherein R$^1$ represents hydroxymethyl may be treated with carbon tetrabromide and triphenylphosphine to afford the corresponding compound of formula I wherein R$^1$ represents bromomethyl, which may then be reacted (typically in situ) with the sodium salt of imidazole or 1H-[1,2,4]triazole to provide a compound of formula I wherein R$^1$ represents imidazol-1-ylmethyl or [1,2,4]triazol-1-ylmethyl respectively; or with the sodium salt of 1H-[1,2,3]triazole to provide a mixture of compounds of formula I wherein R$^1$ represents [1,2,3]triazol-1-ylmethyl and [1,2,3]triazol-2-ylmethyl; or with morpholine to provide a compound of formula I wherein R$^1$ represents morpholin-4-ylmethyl. A compound of formula I wherein Z is substituted with methoxy may be converted to the corresponding compound wherein Z is substituted with hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$-]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000-4000 dpm for total counts and less than 200 dpm for non-specific binding if using liquid scintillation counting, or 1500-2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human $GABA_A$ receptor of 100 nM or less.

EXAMPLE 1

8-Fluoro-3-[3-(pyridin-3-yl)phenyl]imidazo[1,2-α]pyridine n-Butyllithium (2.5 M in hexanes; 230 ml, 0.57 mol) was added to a solution of 1,4-diazabicyclo[2.2.2]octane (pre-dried by azeotropic removal of water with toluene) (63.8 g, 0.57 mol) in $Et_2O$ (2.5 l) holding the temperature between −20 and −30° C. After stirring for 1 h, the temperature was adjusted to −65° C. and a solution of 3-fluoropyridine (50.0 g, 0.52 mol) in $Et_2O$ (250 ml) was added dropwise over 10 min and the mixture stirred for a further 1 h. A solution of hexachloroethane (136.5 g, 0.58 mol) in $Et_2O$ (350 ml) was then added dropwise over 15 min, holding the temperature below −60° C. and the mixture was stirred for 2 h, allowing the temperature to rise to −40° C. The reaction was quenched by addition of saturated aqueous $NH_4Cl$ solution (250 ml), warmed to ambient temperature and separated. The aqueous phase was extracted with $Et_2O$ (2×250 ml) and the combined organics washed with further saturated aq. $NH_4Cl$ (250 ml), dried over anhydrous $MgSO_4$ and concentrated in vacuo. The residue was diluted with isohexane (150 ml) and washed with 2 N hydrochloric acid (3×100 ml), followed by 37% hydrochloric acid (3×50 ml). The acid washings were then extracted with isohexane (3×100 ml), basified to pH 14 by careful addition of 4 N aqueous NaOH solution (500 ml) and re-extracted with $CH_2Cl_2$ (3×150 ml). The organic fractions were dried over anhydrous $MgSO_4$ and concentrated in vacuo. The residue was purified by distillation (bp 74-82° C., 1 atm) to afford 2-chloro-3-fluoropyridine as a straw-coloured oil (42.6 g, 63%): $\delta_H$ (400 MHz, $CDCl_3$) 7.25-7.30 (1H, m), 7.47-7.51 (1H, m), 8.24 (1H, dd, J 0.8 and 4.7); m/z (ES$^+$) 132 (100%, [MH]$^+$).

A mixture of 2-chloro-3-fluoropyridine (21.0 g, 0.16 mol), benzophenone imine (32.3 g, 0.18 mol), $Cs_2CO_3$ (73.0 g, 0.23 mol), BINAP (5.96 g, 9.6 mmol), palladium(II) acetate (1.45 g, 6.4 mmol) and toluene (370 ml) were heated to 95° C. for 42 h, then cooled, filtered and the residue extracted with further toluene (2×210 ml). The filtrate was washed with 0.5 N hydrochloric acid (200 ml) and saturated aqueous $NaHCO_3$ (200 ml), dried over anhydrous $MgSO_4$ and concentrated in vacuo, affording crude benzhydrylidene(3-fluoropyridin-2-yl)amine as a brown oil (49.4 g) which was used directly without further purification: m/z (ES$^+$) 277 (100%, [MH]$^+$).

A mixture of crude benzhydrylidene(3-fluoropyridin-2-yl)amine (49.4 g), 2-bromoacetaldehyde diethyl acetal (56 ml, 0.37 mol), 48% hydrobromic acid (20 ml) and water (20 ml) were heated to 90° C. for 20 min. On cooling, the mixture was diluted with isopropanol (450 ml), $NaHCO_3$ (68 g) was added cautiously, and the mixture filtered. The residue was washed with further isopropanol (450 ml) and the combined organics were stirred and heated to 50° C. for 18 h. On cooling, the solution was concentrated in vacuo and azeotroped with EtOAc (2×440 ml). The remaining mixture was suspended in EtOAc (400 ml), filtered and the residue washed with further EtOAc until the filtrate ran clear (1 l). The solid orange-coloured residue was then suspended between water (100 ml) and EtOAc (220 ml) and the aqueous phase pH adjusted to 8-9 by addition of saturated aqueous $NaHCO_3$ solution (450 ml). The phases were separated and the aqueous extracted with further EtOAc (2×220 ml). The combined organic extracts were dried over anhydrous $MgSO_4$ and concentrated in vacuo affording crude 8-fluoroimidazo[1,2-α]pyridine. Purification was achieved by dissolving the crude material in EtOAc (1 l) and extracting with 2 N hydrochloric acid (5×50 ml). The acid washings were back-extracted with EtOAc (3×100 ml), adjusted to pH 11-12 using 4 N aqueous sodium hydroxide solution and re-extracted with EtOAc (5×100 ml). The combined organic fractions were washed with brine, dried over anhydrous $MgSO_4$ and concentrated in vacuo to afford 8-fluoroimidazo[1,2-α]pyridine (11.4 g, 76% from 2-chloro-3-fluoropyridine): $\delta_H$ (400 MHz, $CDCl_3$) 6.69-6.74 (1H, m), 6.84-6.87 (1H, m), 7.65-7.66 (2H, m), 7.97 (1H, dd, J 1.0 and 6.8); m/z (ES$^+$) 137 (100%, [MH]$^+$).

A solution of bromine in MeOH, saturated with KBr (0.86 M, 1.0 ml, 0.86 mmol) was added to a cooled, stirred solution of 8-fluoroimidazo[1,2-α]pyridine (118 mg, 0.86 mmol) and NaOAc (85 mg, 1.04 mmol) in methanol saturated with KBr (1.6 ml). After 2 min, the solution was poured into water (50 ml) and the resulting yellow solution extracted with $CH_2Cl_2$ (3×50 ml). The combined organic fractions were dried over anhydrous $Na_2SO_4$ and concentrated in vacuo, yielding 3-bromo-8-fluoroimidazo[1,2-α]pyridine as a yellow solid (155 mg, 83%), used without further purification: $\delta_H$ (400 MHz, $CDCl_3$) 6.86-6.91 (1H, m), 6.95-6.99 (1H, m), 7.65 (1H, s), 7.98 (1H, dd, J 0.8 and 6.7); m/z (ES$^+$) 217 (100%, [MH]$^+$), 215 (100).

3-Bromo-8-fluoroimidazo[1,2-α]pyridine, 3-[3-(5,5-dimethyl-[1,3,2]dioxaborinan-2-yl)phenyl]pyridine (prepared as described in WO 01/90108), tetrakis(triphenylphosphine)palladium(0) (42 mg, 0.036 mmol), THF (3.6 ml) and 2 M aqueous $Na_2CO_3$ solution were combined and the vigorously stirred mixture heated to 75° C. for 16 h. After cooling, the mixture was partitioned between 1 N aqueous NaOH solution (20 ml) and $CH_2Cl_2$ (20 ml) and the aqueous phase extracted with further $CH_2Cl_2$ (20 ml). The combined organics were dried over anhydrous $Na_2SO_4$ and concentrated in vacuo, and the residue purified by column chromatography (silica; 2% EtOH/EtOAc) to afford the title imidazopyridine as a white amorphous solid (96 mg, 47%): $\delta_H$ (400 MHz; DMSO) 6.93-6.98 (1H, m), 7.21-7.24 (1H, m), 7.51-7.54 (1H, m), 7.68-7.76 (2H, m), 7.82 (1H, t, J 1.6), 7.94 (1H, s), 8.01 (1H, t, J 1.6), 8.19-8.22 (1H, m), 8.54 (1H, dd, J 0.8 and 7.0), 8.62 (1H, dd, J 1.6 and 4.7), 9.02 (1H, dd, J 0.8 and 2.3); m/z (ES$^+$) 290 (30%, [MH]$^+$), 166 (100).

EXAMPLE 2

2-[8-Fluoro-3-[4-fluoro-3-(pyridin-3-yl)phenyl]imidazo[1,2-α]-pyridin-7-yl]propan-2-ol A mixture of 2-bromo-1-fluoro-4-nitrobenzene (prepared according to the procedure of Groweiss in Org. Proc. Res. Dev., 2000, 4(i), 30-33) (66 g, 300 mmol), KOAc (58.9 g, 600 mmol), bis(pinacolato)diboron (83.8 g, 330 mmol) and dichloro[1,1'-bis(diphenylphosphino)ferrocene]palladium (II) dichloromethane adduct (7.35 g, 9 mmol) in 1,4-dioxane (900 ml containing 18 ml DMSO) was degassed with nitrogen for 1 h then heated at 90° C. for 14 h. The reaction was cooled to ambient temperature, filtered, the filter-cake washed with $Et_2O$ and the filtrate concentrated in vacuo. The residue was stirred with 2 N aqueous NaOH solution (1 l) for 45 min and then filtered. The filtrate was extracted with $Et_2O$ (2×750 ml) and the organics discarded. The aqueous component was cooled to 0° C. then treated with 36% hydrochloric acid (ca. 175 ml) added dropwise over 15 min until pH 5. The resulting precipitate was allowed to stand at 0° C. for 2 h then filtered and washed with ice-cold water. The sand-coloured solid was dried under vacuum (300 mmHg) over phosphorus pentoxide to afford 2-(2-fluoro-5-nitrophenyl)-4,4,5,5-tetramethyl-[1,3,2]dioxaborolane (76.1 g, 95%): $\delta_H$ (400 MHz, CDCl$_3$) 1.38 (12H, s), 7.17 (1H, dd, J 9 and 9), 8.32 (1H, ddd, J 9, 5 and 3), 8.64 (1H, dd, J 5 and 3).

A slurry of 3-bromopyridine (19 g, 120 mmol), 2-(2-fluoro-5-nitrophenyl)-4,4,5,5-tetramethyl-[1,3,2]dioxaborolane (40 g, 150 mmol) and KF (23 g, 396 mmol) in THF (600 ml) and water (30 ml) was degassed with nitrogen for 10 min, then treated with tris(dibenzylideneacetone)-dipalladium(0) (2.2 g, 2.4 mmol) followed by tri-tert-butylphosphine (0.2 M solution in 1,4-dioxane; 2.4 ml, 0.48 mmol), and the reaction was stirred mechanically at ambient temperature for 30 min. The mixture was then heated at 50° C. for 1 h before being cooled to ambient temperature. The reaction was poured into ice-cold 0.5 N aqueous NaOH solution and stirred for 1 h. The solid product was collected by filtration, washed with water, allowed to dry under suction, then washed with isohexane and dried to give 3-(2-fluoro-5-nitrophenyl)pyridine as a grey solid (26.2 g, contaminated with dibenzylideneacetone): $\delta_H$ (400 MHz, CDCl$_3$) 7.37 (1H, t, J 9), 7.45 (1H, ddd, J 8, 5 and 1), 7.89-7.93 (1H, m), 8.28-8.33 (1H, m), 8.40 (1H, dd, J 7 and 3), 8.71 (1H, d, J 4), 8.84 (1H, s).

A suspension of 3-(2-fluoro-5-nitrophenyl)pyridine (26 g, 119 mmol) in EtOH (200 ml) and EtOAc (200 ml) was treated with PtO$_2$ (1.35 g, 6 mmol) then exposed to 50 psi hydrogen until uptake ceased (circa 3 hours). The reaction was filtered through glass-microfibre filter paper and concentrated to gave 3-(2-fluoro-5-aminophenyl)pyridine (22.4 g) as a dark oil which solidified on standing: $\delta_H$ (360 MHz, CDCl$_3$) 3.65 (2H, s), 6.65-6.72 (2H, m), 6.99 (1H, dd, J 9 and 9), 7.33-7.37 (1H, m), 7.84-7.86 (1H, m), 8.58 (1H, d, J 4), 8.76 (1H, m).

A solution of 3-(2-fluoro-5-aminophenyl)pyridine (22.4 g, 119 mmol) in 1,4-dioxane (40 ml) was treated with a solution of 48% aqueous hydrobromic acid (500 ml). The resulting suspension was cooled to 0° C. before being treated dropwise over 20 min with an aqueous solution of NaNO$_2$ (9.5 g, 137 mmol) in water (30 ml) keeping the internal temperature <5° C. After stirring at 0° C. for 2 h, a cooled (0° C.) solution of CuBr (25.6 g, 179 mmol) in 48% aqueous hydrobromic acid (150 ml) was added to the reaction which was then stirred at 0° C. for 10 min before heating at 50° C. for 20 min. The reaction was cooled to ambient temperature, diluted with ice-cold water (500 ml), then treated with ice-cold aqueous 33% ammonium hydroxide solution until pH 8-9 (ca. 750 ml). After stirring for 20 min the product was extracted into EtOAc (600 ml), the organics were washed with water, brine (300 ml), dried over anhydrous NaSO$_4$, filtered and pre-adsorbed onto silica. Purification by column chromatography [silica; 20-50% EtOAc/isohexane (containing 1% MeOH and 1% triethylamine)] gave 3-(5-bromo-2-fluorophenyl)pyridine as a white solid (22 g, 73% for sequence): 8H (360 MHz, CDCl$_3$) 7.09 (1H, dd, J 9 and 1), 7.37-7.40 (1H, m), 7.46-7.51 (1H, m), 7.56-7.59 (1H, m), 7.83-7.86 (1H, m), 8.63-8.65 (1H, m), 8.77-8.79 (1H, m).

3-(5-Bromo-2-fluorophenyl)pyridine (21 g, 83 mmol), KOAc (16.4 g, 167 mmol) and bis(pinacolato)diboron (23.3 g, 92 mmol) were dissolved in 1,4-dioxane (250 ml) and DMSO (5 ml) and the mixture degassed with nitrogen for 1 h. Dichloro[1,1'-bis(diphenylphosphino)ferrocene]-palladium(II) dichloromethane adduct (2 g, 2.5 mmol) was added and the mixture heated at 90° C. for 18 h. The mixture was cooled to ambient temperature, filtered and the filter cake washed with Et$_2$O. The filtrate was evaporated to dryness and the residue stirred with ice-cold 2 N aqueous NaOH solution (500 ml) for 20 min. The aqueous mixture was filtered and the filtrate washed with Et$_2$O (2×300 ml). The organics were discarded and the aqueous phase cooled to 0° C. before adjusting the pH to 8 by addition of 36% hydrochloric acid. This gave a gummy solid, which was extracted into Et$_2$O (500 ml). The solid product at the water-Et$_2$O interface was collected by filtration and dried to afford 4-fluoro-3-(pyridin-3-yl)boronic acid as a buff-coloured solid (3.7 g): $\delta_H$ (400 MHz, DMSO) 7.32 (1H, dd, J 11 and 8), 7.53 (1H, dd, J 8 and 5), 7.85-7.90 (1H, m), 7.97-8.02 (2H, m), 8.21 (2H, s), 8.61 (1H, d, J 4), 8.78 (1H, s).

A mixture of lithium diisopropylamide (2 M in heptane/THF/ethylbenzene, stabilised with 0.5% w/w LiBr; 1.9 ml, 3.8 mmol) and THF (3 ml) was cooled to −78° C. and a solution of 2-chloro-3-fluoropyridine (500 mg, 3.8 mmol) in THF (3 ml) was added dropwise over 1 min. After 2 h, acetone (pre-dried twice over activated 4 Å molecular sieves) was added dropwise and the mixture allowed to warm to ambient temperature, then quenched with saturated aqueous NH$_4$Cl solution (10 ml) and extracted with EtOAc (50 ml). The organic phase was dried over anhydrous MgSO$_4$ and concentrated in vacuo. The crude material was purified by column chromatography (silica; 10-20% EtOAc/isohexane) to afford 2-(2-chloro-3-fluoropyridin-4-yl)propan-2-ol (687 mg, 95%): $\delta_H$ (360 MHz, CDCl$_3$) 1.66 (6H, s), 7.53 (1H, m), 8.16 (1H, m); m/z (ES$^+$) 190 (100%, [MH]$^+$).

2-(2-Chloro-3-fluoropyridin-4-yl)propan-2-ol (687 mg, 3.6 mmol) was converted to 2-(8-fluoroimidazo[1,2-α]pyridin-7-yl)propan-2-ol (240 mg, 34%) as described in Example 1: $\delta_H$ (360 MHz, CDCl$_3$) 1.71 (6H, s), 7.14 (1H, t, J 6.8), 7.58-7.61 (2H, m), 7.91 (1H, d, J 7.1); m/z (ES$^+$) 195 (100%, [MH]$^+$).

2-(8-Fluoroimidazo[1,2-α]pyridin-7-yl)propan-2-ol (1.00 g, 5.2 mmol) was brominated as described in Example 1, affording 2-(3-bromo-8-fluoroimidazo[1,2-α]pyridin-7-yl)propan-2-ol (637 mg, 45%): $\delta_H$ (360 MHz, CDCl$_3$) 1.72 (6H, s), 7.32 (1H, t, J 6.9), 7.59 (1H, s), 7.89 (1H, d, J 7.3); m/z (ES$^+$) 275 (100%, [MH]$^+$), 273 (100).

Hünig's base (0.44 ml, 3.8 mmol) and triethylsilyl trifluoromethanesulfonate (0.57 ml, 2.6 mmol) were added sequentially to a cold (−78° C.), stirred solution of 2-(3-bromo-8-fluoroimidazo[1,2-α]pyridin-7-yl)propan-2-ol (637 mg, 2.3 mmol) in CH$_2$Cl$_2$ (13 ml) and the solution warmed to ambient temperature. The mixture was partitioned between CH$_2$Cl$_2$ (50 ml) and water (50 ml) and the organic phase dried over anhydrous MgSO$_4$, filtered through a short plug of silica (eluent CH$_2$Cl$_2$) and concentrated to afford 3-bromo-8-fluoro-7-[2-(triethylsilyloxy)prop-2-yl]imidazo[1,2-α]pyridine (906 mg, quant.): $\delta_H$ (360 MHz, CDCl$_3$) 0.70 (6H, q, J 7.8), 0.99 (9H, t, J 7.8), 1.71 (6H, s), 7.32 (1H, t, J 6.9), 7.59 (1H, s), 7.88 (1H, d, J 7.3).

3-Bromo-8-fluoro-7-[2-(triethylsilyloxy)prop-2-yl]imidazo[1,2-α]pyridine was coupled with 4-fluoro-3-(pyridin-3-yl)phenylboronic acid as described in Example 1 and then deprotected by treatment with an ethanolic solution of 37% hydrochloric acid (5 drops in 2 ml of ethanol). After 18 h, the solution was concentrated in vacuo and purified by column chromatography on silica, to afford the title compound as a white amorphous solid: $\delta_H$ (360 MHz, CDCl$_3$) 1.74 (6H, s), 7.20 (1H, t, J 7.0), 7.26-7.44 (2H, m), 7.54-7.62 (2H, m), 7.71 (1H, s), 7.90-7.93 (2H, m), 8.05 (1H, d, J 7.3), 8.65-8.66 (1H, m), 8.85 (1H, s); m/z (ES$^+$) 366 (100%, [MH]$^+$).

EXAMPLE 3

2'-Fluoro-5'-[8-fluoro-7-(2-hydroxyprop-2-yl)imidazo[1,2-α]pyridin-3-yl]biphenyl-2-carbonitrile A mixture of 2-bromobenzonitrile (34.6 g, 190 mmol) and 2-(2-fluoro-5-nitrophenyl)-4,4,5,5-tetramethyl-[1,3,2]dioxaborolane (76.1 g, 285 mmol) were coupled as described in Example 2 to afford 2'-fluoro-5'-nitrobiphenyl-2-carbonitrile as a beige solid (46 g, 100%): $\delta_H$ (360 MHz, CDCl$_3$) 7.37-7.42 (1H, m), 7.53 (1H, d, J 8), 7.59 (1H, td, J 8 and 1), 7.75 (1H, td, J 8 and 1), 7.83 (1H, dd, J 8 and 1), 8.35-8.39 (2H, m).

A cooled (0° C.) suspension of 2'-fluoro-5'-nitrobiphenyl-2-carbonitrile (24.2 g, 100 mmol) in EtOH (150 ml) and THF (150 ml) was treated with SnCl$_2$2H$_2$O (67.7 g, 300 mmol) and the mixture was stirred to ambient temperature over 12 h. The solvent was removed in vacuo and the residue treated with ice-cold aqueous 2 N NaOH solution (750 ml). The resulting slurry was stirred for 60 min then extracted with CH$_2$Cl$_2$ (2×400 ml). The organics were combined, washed with water, brine, dried over anhydrous MgSO$_4$, filtered and concentrated to give a red solid. Crystallisation from toluene gave 5'-amino-2'-fluorobiphenyl-2-carbonitrile as a cream-coloured solid (16 g, 75%): $\delta_H$ (400 MHz, CDCl$_3$) 3.65 (2H, br), 6.67-6.73 (2H, m), 7.00 (1H, t, J 9), 7.44-7.49 (2H, m), 7.64 (1H, td, J 9 and 2), 7.75 (1H, dd, J 8 and 2); m/z (ES$^+$) 213 (100%, [MH]$^+$).

5'-Amino-2'-fluorobiphenyl-2-carbonitrile (7.85 g, 37 mmol) was bromo-deaminated as described in Example 2 to afford 5'-bromo-2'-fluorobiphenyl-2-carbonitrile as a white solid (6.5 g, 64%): $\delta_H$ (400 MHz, CDCl$_3$) 7.09-7.14 (1H, m), 7.45-7.57 (4H, m), 7.66 (1H, td, J 8 and 2), 7.77 (1H, dd, J 8 and 2).

A mixture of 5'-bromo-2'-fluorobiphenyl-2-carbonitrile (1.1 g, 4 mmol), KOAc (1.18 g, 12 mmol) and bis(pinacolato)diboron (1.17 g, 4.6 mmol) was dissolved in 1,4-dioxane containing 1% v/v DMSO (15 ml) and this solution was degassed with nitrogen for 5 min. Dichloro[1,1'-bis(diphenylphosphino)ferrocene]palladium(II) dichloromethane adduct (98 mg, 0.12 mmol) was then added and the mixture heated at 90° C. for 16 h. After cooling to ambient temperature the reaction was partitioned between EtOAc and water. The organic phase was washed with brine, dried over anhydrous MgSO$_4$, filtered and pre-adsorbed onto silica. Purification by chromatography (silica; 2-10% EtOAc/isohexane) gave a colourless oil which crystallised on standing to furnish 2'-fluoro-5'-(4,4,5,5-tetramethyl-[1,3,2]dioxaborolan-2-yl)biphenyl-2-carbonitrile as a white solid (1.3 g, 100%): $\delta_H$ (400 M, CDCl$_3$) 1.34 (12H, s), 7.21 (1H, dd, J 10 and 8), 7.45-7.52 (2H, m), 7.65 (1H, td, J 8 and 2), 7.74-7.78 (1H, m), 7.83 (1H, dd, J 8 and 2), 7.88 (1H, ddd, J 8, 5 and 2).

2'-Fluoro-5'-(4,4,5,5-tetramethyl-[1,3,2]dioxaborolan-2-yl)biphenyl-2-carbonitrile was coupled with 3-bromo-8-fluoro-7-[2-(triethylsilyloxy)-prop-2-yl]imidazo[1,2-α]pyridine as described in Example 1 and deprotected as described in Example 2 to afford the title imidazopyridine as an amorphous white solid: $\delta_H$ (360 MHz, CDCl$_3$) 1.73 (6H, s), 7.20 (1H, t, J 7.0), 7.39 (1H, t, J 8.8), 7.54 (1H, dt, J 1.2 and 7.8), 7.59-7.64 (3H, m), 7.68-7.72 (2H, m), 7.83 (1H, d, J 6.8), 8.25 (1H, d, J 7.3); m/z (ES$^+$) 390 (100%, [MH]$^+$).

EXAMPLE 4

7-Chloro-8-fluoro-3-[4-fluoro-3-(pyridin-3-yl)phenyl]imidazo[1,2-α]pyridine

A mixture of lithium diisopropylamide (2 M in heptane/THF/ethylbenzene, stabilised with 0.5% w/w LiBr; 3.8 ml, 7.6 mmol) and THF (3 ml) was cooled to −78° C. and a solution of 2-chloro-3-fluoropyridine (1.0 g, 7.6 mmol) in THF (2 ml) was added dropwise over 1 min. After 2 h, a solution of hexachloroethane (2.0 g, 8.4 mmol) in THF (3 ml) was added dropwise and stirring continued for 2 h before quenching with saturated aqueous NH$_4$Cl solution (20 ml) and extraction of the reaction product with EtOAc (100 ml). The organic phase was dried over anhydrous MgSO$_4$ and concentrated in vacuo. The crude material was purified by column chromatography (silica; 15% Et$_2$O/isohexane) to afford 2,4-dichloro-3-fluoropyridine (795 mg, 63%): $\delta_H$ (400 MHz, CDCl$_3$) 7.34 (1H, t, J 5.1), 8.13 (1H, d, J 5.1); m/z (ES$^+$) 166 (100%, [MH]$^+$).

2,4-Dichloro-3-fluoropyridine (495 mg, 3.0 mmol) was converted to 7-chloro-8-fluoroimidazo[1,2-α]pyridine (225 mg, 44%) as described in Example 1: $\delta_H$ (400 MHz, CDCl$_3$) 6.80 (1H, dd, J 5.9, 7.0), 7.63 (1H, dd, J 1.2, 2.7), 7.66 (1H, s), 7.91 (1H, dd, J 1.2, 7.0); m/z (ES$^+$) 171 (100%, [MH]$^+$).

7-Chloro-8-fluoroimidazo[1,2-α]pyridine (115 mg, 0.67 mmol) was brominated as described in Example 1, affording 3-bromo-7-chloro-8-fluoroimidazo[1,2-α]pyridine (162 mg, 96%): $\delta_H$ (400 MHz, CDCl$_3$) 6.95 (1H, dd, J 5.9, 7.0), 7.64 (1H, s), 7.91 (1H, dd, J 0.8, 7.0); m/z (ES$^+$) 249 (75%, [MH]$^+$), 251 (100), 253 (25).

3-Bromo-7-chloro-8-fluoroimidazo[1,2-α]pyridine (45 mg, 0.18 mmol) was coupled with 4-fluoro-3-(pyridin-3-yl)phenylboronic acid (49 mg, 0.19 mmol), as described in Example 1, to afford the title compound as a white amorphous solid (49 mg, 80%): $\delta_H$ (400 MHz, DMSO) 7.10 (1H, t, J 7.0), 7.54-7.61 (2H, m), 7.77-7.81 (1H, m), 7.92 (1H, dd, J 2.3, 7.4), 7.94 (1H, s), 8.09-8.12 (1H, m), 8.52 (1H, dd, J 1.0, 7.2), 8.65-8.66 (1H, m), 8.88 (1H, s); m/z (ES$^+$) 342 (100%, [MH]$^+$).

EXAMPLE 5

5'-[7-chloro-8-fluoroimidazo[1,2-α]pyridin-3-yl]-2'-fluorobiphenyl-2-carbonitrile 3-Bromo-7-chloro-8-fluoroimidazo[1,2-α]pyridine (70 mg, 0.28 mmol) was coupled with 2'-fluoro-5'-(4,4,5,5-tetramethyl-[1,3,2]dioxaborolan-2-yl)biphenyl-2-carbonitrile (109 mg, 0.34 mmol), as described in Example 1, to afford the title compound as a white amorphous solid (72 mg, 71%): $\delta_H$ (400 MHz, DMSO) 7.11 (1H, t, J 7.0), 7.60-7.70 (2H, m), 7.78 (1H, s), 7.85-7.89 (3H, m), 7.93 (1H, s), 8.04 (1H, dd, J 0.8, 7.8), 8.52 (1H, dd, J 1.0, 7.2); m/z (ES$^+$) 366 (100%, [MH]$^+$).

EXAMPLE 6

4.2'-Difluoro-5'-[8-fluoro-7-(1-hydroxy-1-methylethyl)imidazo[1,2-α]pyridin-3-yl]biphenyl-2-carbonitrile 2-Bromo-5-fluorobenzonitrile was coupled to 2-(2-fluoro-5-nitrophenyl)-4,4,5,5-tetramethyl-[1,3,2]dioxaborolane as described in Example 2 to give 4,2'-difluoro-5'-nitrobiphenyl-2-carbonitrile as a black solid: $\delta_H$ (360 MHz, CDCl$_3$) 7.38-7.56 (4H, m), 8.33-8.40 (2H, m).

4,2'-Difluoro-5'-nitrobiphenyl-2-carbonitrile was reduced using the procedure described in Example 2 to give 5'-amino-4,2'-difluorobiphenyl-2-carbonitrile: $\delta_H$ (360 MHz, CDCl$_3$) 3.66 (2H, s), 6.66-6.70 (1H, m), 6.71-6.74 (1H, m), 7.00 (1H, dd, J 9, 9), 7.33-7.38 (1H, m), 7.44-7.49 (1H, m).

5'-Amino-4,2'-difluorobiphenyl-2-carbonitrile was bromo-deaminated using the procedure described in Example 2 to give 5'-bromo-4,2'-difluorobiphenyl-2-carbonitrile as a pale brown solid: $\delta_H$ (360 MHz, CDCl$_3$) 7.11 (1H, dd, J 9, 9), 7.37-7.58 (5H, m).

A mixture of 2-(8-fluoroimidazo[1,2-α]pyridin-7-yl)propan-2-ol (97 mg, 0.5 mmol), 5'-bromo-4,2'-difluorobiphenyl-2-carbonitrile (177 mg, 0.6 mmol) and Cs$_2$CO$_3$ (538 mg, 1.65 mmol) in 1,4-dioxane (3 ml) was degassed with nitrogen for 30 min. Tetrakis(triphenylphosphine)-palladium(0) (29 mg, 0.03 mmol) was added and the mixture heated under reflux for 48 h. On cooling, the mixture was partitioned between ethyl acetate (100 ml) and water (100 ml). The organics were washed with water (100 ml) and brine (50 ml), dried over anhydrous sodium sulfate, filtered and concentrated in vacuo to give an orange oil. The oil was purified by flash column chromatography on silica, eluting with dichloromethane (+1% 0.880 ammonia solution) on a gradient of methanol (1-3%). Collecting appropriate fractions followed by trituration with diethyl ether/isohexane (1:1, 5 ml) gave the title imidazopyridine as an off-white amorphous solid (67 mg, 33%): $\delta_H$ (360 MHz, CDCl$_3$) 1.74 (6H, d, J 1.1), 2.06-2.10 (1H, m), 7.20 (1H, t, J 7.0), 7.37-7.45 (2H, m), 7.52-7.64 (4H, m), 7.70 (1H, s), 8.22 (1H, d, J 7.0); m/z (ES$^+$) 408 (100%, [MH]$^+$).

EXAMPLE 7

2-{3-[3-(3,5-Difluoropyridin-2-yl)-4-fluorophenyl-8-fluoroimidazo[1,2-α]pyridin-7-yl}propan-2-ol To a degassed mixture of 3,5-difluoro-2,4,6-tribromopyridine (4.26 g, 12.1 mmol), 2-(2-fluoro-5-nitrophenyl)-4,4,5,5-tetramethyl-[1,3,2]dioxaborolane (2.80 g, 10.4 mmol), aqueous sodium carbonate (10 ml of a 2M solution) and tetrahydrofuran (40 ml) was added tetrakis(triphenylphosphine)palladium(0) (0.67 g). The mixture was then stirred at 55° C. for 48 h under an atmosphere of nitrogen. The reaction mixture was then partitioned between water and ethyl acetate. The organic layer was separated and evaporated and the residue chromatographed on silica gel eluting with isohexane on a gradient of dichloromethane (20-40%) to afford 2,4-dibromo-3,5-difluoro-6-(2-fluoro-5-nitrophenyl)pyridine as a solid (1.21 g): $\delta_H$ (400 Mdz, CDCl$_3$) 7.37 (1H, t, J 9 Hz), 8.38 (1H, m), 8.55 (1H, dd, J 6, 3).

To 2,4-dibromo-3,5-difluoro-6-(2-fluoro-5-nitrophenyl) pyridine (1.20 g, 2.91 mmol) dissolved in dichloromethane (30 ml) was added triethylamine (3 ml) and ethanol (80 ml) followed by 10% palladium on carbon (0.536 g). The mixture was then shaken under an atmosphere of hydrogen gas at 45 psi until complete reaction was indicated by TLC (0.25 to 3.5 h). The catalyst was then removed by filtration through glass microfibre filter paper (GF/A) and the solvent stripped at reduced pressure to afford 3-(3,5-difluoropyridin-2-yl)-4-fluorophenylamine which was used subsequently without further purification: m/z (ES$^+$) 225 (MH$^+$).

To the 3-(3,5-difluoropyridin-2-yl)-4-fluorophenylamine prepared above was added 1,4-dioxane (5 ml) and 48% aqueous hydrogen bromide (15 ml). The solution was cooled to −10° C. and a solution of sodium nitrite (0.252 g) in water (1 ml) was added dropwise with stirring at such a rate as to maintain an internal temperature below −5° C. The mixture was then stirred for a further 1 h at <0° C. before a solution of copper(I) bromide (1.283 g) in 48% aqueous hydrogen bromide (5 ml) was added slowly with stirring to maintain a reaction temperature below 10° C. This mixture was then stirred at 10° C. for 1 h, ambient temperature a further 1 h and then heated at 35° C. for 30 min. The reaction mixture was then cooled in an ice-water bath and 4N aqueous sodium hydroxide (41 ml) was added slowly with stirring, followed by 30% aqueous ammonia (15 ml). The resulting mixture was extracted with ethyl acetate. The organic extract was evaporated and the residue subjected to chromatography on silica gel, eluting with 10% diethyl ether in isohexane, to afford 2-(5-bromo-2-fluorophenyl)-3,5-difluoropyridine (0.48 g) as a colourless solid: m/z (ES$^+$) 288, 290 (MH$^+$).

2-(8-Fluoroimidazo[1,2-α]pyridin-7-yl)propan-2-ol (97 mg, 0.5 mmol) was coupled with 2-(5-bromo-2-fluorophenyl)-3,5-difluoropyridine (173 mg, 0.6 mmol), as described in Example 6, affording the title imidazopyridine as an off-white amorphous solid (35 mg, 17%): $\delta_H$ (360 MHz, CDCl$_3$) 1.74 (6H, s), 2.03 (1H, s), 7.19 (1H, m), 7.33-7.39 (2H, m), 7.60-7.64 (1H, m), 7.71 (1H, s), 7.77 (1H, dd, J 6.7, 2.5), 8.08 (1H, d, J 7.4), 8.49 (1H, d, J 2.1); m/z (ES$^+$) 402 (100%, [MH]$^+$).

EXAMPLE 8

6,2'-Difluoro-5'-[8-fluoro-7-(1-hydroxy-1-methyl)ethyl) imidazo[1,2-α]pyridin-3-yl]biphenyl-2-carbonitrile A mixture of 2,3-difluorobenzonitrile (19.0 g, 137 mmol) and ethanol (200 ml) pre-saturated with ammonia gas was heated at 140° C. in an autoclave for 8 h (terminal pressure 200 psi). The mixture was allowed to cool to ambient temperature and evaporated to dryness. The residue was dissolved in water (400 ml) and extracted with diethyl ether (2×300 ml). The combined organics were washed with water (300 ml) and brine (250 ml), dried over anhydrous magnesium sulfate, filtered and evaporated. Trituration with isohexane (150 ml) afforded 2-amino-3-fluorobenzonitrile (9.8 g, 50%) as an off-white solid: $\delta_H$ (360 MHz, CDCl$_3$) 4.47 (2H, s), 6.65-6.71 (1H, m), 7.14-7.20 (2H, m).

2-Amino-3-fluorobenzonitrile (9.8 g, 71.9 mmol) was bromo-deaminated as described in Example 2 to afford 2-bromo-3-fluorobenzonitrile as a pale brown solid: $\delta_H$ (360 MHz, CDCl$_3$) 7.62-7.68 (1H, m), 7.74-7.85 (1H, ddd, J 9, 9, 1), 7.74-7.85 (1H, ddd, J 8, 1, 1).

2-Bromo-3-fluorobenzonitrile (2.50 g, 12.5 mmol) was coupled to 2-(2-fluoro-5-nitrophenyl)-4,4,5,5-tetramethyl-[1,3,2]dioxaborolane as described in Example 2 to give 6,2'-difluoro-5'-nitrobiphenyl-2-carbonitrile as a black solid: $\delta_H$ (400 z, CDCl$_3$) 7.40-7.44 (1H, m), 7.47-7.52 (1H, m), 7.59-7.67 (2H, m), 8.37-8.44 (2H, m).

6,2'-Difluoro-5'-nitrobiphenyl-2-carbonitrile (3.25 g, 12.5 mmol) was reduced using the procedure described in Example 2 to give 5'-amino-6,2'-difluorobiphenyl-2-carbonitrile as a brown oil: $\delta_H$ (360 MHz, CDCl$_3$) 3.74 (2H, s), 6.68 (1H, m), 6.73-6.77 (1H, m), 7.02 (1H, dd, J 9, 9), 7.37-7.49 (2H, m), 7.56-7.65 (1H, m).

5'-Amino-6,2'-difluorobiphenyl-2-carbonitrile was bromo-deaminated as described in Example 2 to furnish 5'-bromo-6,2'-difluorobiphenyl-2-carbonitrile as a pale brown solid: $\delta_H$ (360 MHz, CDCl$_3$) 7.13 (1H, dd, J 9, 9), 7.37-7.49 (2H, ddd, J 9, 9, 1), 7.57-7.62 (4H, m).

2-(8-Fluoroimidazo[1,2-α]pyridin-7-yl)propan-2-ol (97 mg, 0.5 mmol) was coupled with 5'-bromo-6,2'-difluorobiphenyl-2-carbonitrile (177 mg, 0.6 mmol), as described in Example 6, affording the title imidazopyridine as a white amorphous solid (90 mg, 44%): $\delta_H$ (360 MHz, CDCl$_3$) 1.73

(6H, d, J 0.6), 2.05-2.08 (1H, m), 7.19 (1H, t, J 7.0), 7.38-7.68 (6H, m), 7.71 (1H, s), 8.22 (1H, d, J 7.0); m/z (ES$^+$) 408 (100%, [MH]$^+$).

EXAMPLE 9

2-{2-Fluoro-5-[8-fluoro-7-(1-hydroxy-1-methylethyl)imidazo[1,2-α]pyridin-3-yl]phenyl}nicotinonitrile 2-Chloronicotinonitrile (0.80 g, 5.8 mmol) was coupled to 2-(2-fluoro-5-nitrophenyl)-4,4,5,5-tetramethyl-[1,3,2]dioxaborolane (2 g, 7.49 mmol) using the method in Example 2. Purification by chromatography on silica gel eluting with dichloromethane gave 2-(2-fluoro-5-nitrophenyl)-nicotinonitrile as a yellow solid: $\delta_H$ (360 MHz, CDCl$_3$) 8.97 (1H, dd, J 5, 2), 8.56 (1H, dd, J 6, 3), 8.40-8.45 (1H, m), 8.15 (1H, dd, J 8, 2), 7.55 (1H, dd, J 8, 5), 7.43 (1H, dd, J 9, 9); m/z (ES$^+$) 244 (M$^+$+H).

2-(2-Fluoro-5-nitrophenyl)nicotinonitrile (1.2 g, 4.9 mmol) was reduced by the method described in Example 2. Purification by chromatography on silica gel eluting with dichloromethane containing 1% methanol gave 2-(5-amino-2-fluorophenyl)nicotinonitrile as an orange oil: $\delta_H$ (360 MHz, CDCl$_3$) 8.88 (1H, dd, J 5, 2), 8.07 (1H, dd, J 8, 2), 7.42 (1H, dd, J 8, 5), 7.04 (1H, dd, J 9, 9), 6.85 (1H, dd, J 6, 3), 6.76-6.81 (1H, m); m/z (ES$^+$) 214 (M$^+$+H).

2-(5-Amino-2-fluorophenyl)nicotinonitrile (1.0 g, 4.7 mmol) was bromo-deaminated by the method described in Example 2 to give 2-(5-bromo-2-fluorophenyl)nicotinonitrile as a white powder: $\delta_H$ (360 MHz, CDCl$_3$) 8.92 (1H, dd, J 5, 1), 8.10 (1H, dd, J 8, 2), 7.74 (1H, dd, J 6, 2), 7.59-7.64 (1H, m), 7.48 (1H, dd, J 8, 5), 7.15 (1H, dd, J 9, 9).

2-(8-Fluoroidaz[1,2-α]pyridin-7-yl)propan-2-ol (97 mg, 0.5 mmol) was coupled with 2-(5-bromo-2-fluorophenyl)nicotinonitrile (177 mg, 0.6 mmol), as described in Example 6, affording the title imidazopyridine as an off-white amorphous solid (60 mg, 31%): $\delta_H$ (360 z, CDCl$_3$) 1.74 (6H, d, J 0.7), 2.07 (1H, s), 7.20 (1H, t, J 7.0), 7.42 (1H, t, J 9.1), 7.51 (1H, dd, J 7.7, 4.9), 7.66-7.70 (1H, m), 7.73 (1H, s), 7.79 (1H, dd, J 6.7, 2.1), 8.13-8.16 (2H, m), 8.95 (1H, dd, J 4.9, 1.8); m/z (ES$^+$) 391 (100%, [MH]$^+$).

EXAMPLE 10

3.2'-Difluoro-5'-[8-fluoro-7-(1-hydroxy-1-methylethyl)imidazo[1,2-α]pyridin-3-yl]biphenyl-2-carbonitrile A mixture of 2,6-difluorobenzonitrile (19.0 g, 137 mmol) and ethanol (200 ml) pre-saturated with ammonia gas was heated at 140° C. in an autoclave for 6 h (terminal pressure 200 psi). The mixture was allowed to cool to ambient temperature, evaporated to dryness and triturated with water (200 ml). The solid was filtered and left to air-dry to afford 2-amino-6-fluorobenzonitrile (18.0 g, 97%) as an off-white solid: $\delta_H$ (360 MHz, CDCl$_3$) 4.53 (3H, s), 6.44-6.52 (2H, m), 7.24-7.30 (1H, m).

2-Amino-6-fluorobenzonitrile (18.0 g, 132 mmol) was dissolved in hot 1,4-dioxane (20 ml), 48% hydrobromic acid (200 ml) was added and the mixture cooled to 0° C. before dropwise addition of sodium nitrite (10.5 g, 152 mmol) in water (20 ml) over 1.5 h. The resulting mixture was stirred at 0° C. for 1.5 h then poured onto a cooled (0° C.) solution of copper(I) bromide (56.8 g, 396 mmol) in 48% hydrobromic acid (50 ml). The solution was stirred at 0° C. for 15 min then heated at 50° C. for 20 min. The mixture was cooled to ambient temperature, diluted with water (1200 ml) and extracted with ethyl acetate (2×400 ml). The combined organics were washed with 10% aqueous ammonia solution (400 ml), water (400 ml) and brine (500 ml), dried over anhydrous magnesium sulphate, filtered and evaporated to give an orange oil. Purification by chromatography on silica gel, eluting with isohexane on a gradient with ethyl acetate (2-4%), gave 2-bromo-6-fluorobenzonitrile (18.5 g, 70%) as a white solid: $\delta_H$ (400 MHz, CDCl$_3$) 7.17-7.23 (1H, ddd, J 8, 8 and 1), 7.44-7.52 (2H, m).

2-Bromo-6-fluorobenzonitrile and 2-(2-fluoro-5-nitrophenyl)-4,4,5,5-tetramethyl-[1,3,2]dioxaborolane were coupled following the procedure in Example 2 to afford 3,2'-difluoro-5'-nitrobiphenyl-2-carbonitrile as a black solid: $\delta_H$ (360 MHz, CDCl$_3$) 7.32-7.44 (3H, m), 7.71-7.77 (1H, m), 8.35-8.41 (2H, m).

3,2'-Difluoro-5'-nitrobiphenyl-2-carbonitrile was reduced following the procedure in Example 2 to give 5'-amino-3,2'-difluorobiphenyl-2-carbonitrile as a brown solid: $\delta_H$ (360 MHz, CDCl$_3$) 3.74 (2H, s), 6.66-6.75 (2H, m), 7.01 (1H, dd, J 9 and 9), 7.19-7.30 (2H, m), 7.59-7.65 (1H, m).

5'-Amino-3,2'-difluorobiphenyl-2-carbonitrile was bromo-de-aminated following the procedure in Example 2 to give 5'-bromo-3,2'-difluorobiphenyl-2-carbonitrile as a white solid: $\delta_H$ (400 MHz, CDCl$_3$) 7.13 (1H, dd, J 9 and 9), 7.27-7.30 (2H, m), 7.53-7.59 (2H, m), 7.64-7.69 (1H, m).

5'-Bromo-3,2'-difluorobiphenyl-2-carbonitrile was converted, following the procedure in Example 2, to 3,2'-difluoro-5'-(5,5-dimethyl-[1,3,2]dioxaborinan-2-yl)biphenyl-2-carbonitrile, a brown oil that crystallised on standing: $\delta_H$ (360 MHz, CDCl$_3$) 1.03 (6H, s), 3.77 (4H, s), 7.17-7.25 (2H, m), 7.30 (1H, d, J 8), 7.59-7.65 (1H, m), 7.81-7.91 (2H, m).

3-Bromo-8-fluoro-7-(1-hydroxy-1-methylethyl)imidazo[1,2-α]pyridine (0.10 g, 0.36 mmol) and 3,2'-difluoro-5'-(5,5-dimethyl-[1,3,2]dioxaborinan-2-yl)biphenyl-2-carbonitrile (0.16 g, 0.47 mmol) were coupled following the procedure in Example 1 to afford 3,2'-difluoro-5'-[8-fluoro-7-(1-hydroxy-1-methylethyl)imidazo[1,2-α]pyridin-3-yl]biphenyl-2-carbonitrile as a white amorphous solid (110 mg, 74%): $\delta_H$ (360 MHz, CDCl$_3$) 1.73 (6H, s), 2.10 (1H, s), 7.21 (1H, dd, J 7 and 7), 7.30 (1H, dd, J 8 and 8), 7.38-7.44 (2H, m), 7.61-7.72 (4H, m), 8.23 (1H, d, J 7); m/z (ES$^+$) 408 (M$^+$+H).

EXAMPLE 11

4-Fluoro-3'-[8-fluoro-7-(1-hydroxy-1-methylethyl)imidazo[1,2-α]pyridin-3-yl]biphenyl-2-carbonitrile 2-Bromo-5-fluorobenzonitrile and 3-nitrophenylboronic acid were coupled following the procedure in Example 2 to afford 4-fluoro-3'-nitro-biphenyl-2-carbonitrile as a black solid: $\delta_H$ (360 MHz, CDCl$_3$) 7.39-7.48 (2H, m), 7.52-7.64 (1H, m), 7.71 (1H, dd, J 8 and 8), 7.89 (1H, d, J 8), 8.33-8.37 (2H, m).

4-Fluoro-3'-nitrobiphenyl-2-carbonitrile was reduced following the procedure in Example 2 to give 3'-amino-4-fluorobiphenyl-2-carbonitrile as a brown solid: $\delta_H$ (360 MHz, CDCl$_3$) 6.76 (1H, ddd, J 8, 2 and 2), 6.80 (1H, dd, J 2 and 2), 6.87 (1H, ddd, J 8, 1 and 1), 7.27 (1H, dd, J 8 and 8), 7.35 (1H, ddd, J 8, 8 and 3), 7.41-7.51 (2H, m).

3'-Amino-4-fluorobiphenyl-2-carbonitrile was bromo-deaminated following the procedure in Example 2 to give 3'-bromo-4-fluorobiphenyl-2-carbonitrile as a white solid: $\delta_H$ (400 MHz, CDCl$_3$) 7.35-7.40 (2H, m), 7.46-7.50 (3H, m), 7.59 (1H, dd, J 2 and 1), 7.64 (1H, dd, J 2 and 2).

3'-Bromo-4-fluorobiphenyl-2-carbonitrile was converted, following the procedure in Example 2, to 4-fluoro-3'-(4,4,5,5-tetramethyl-[1,3,2]dioxaborolan-2-yl)biphenyl-2-carbonitrile, a brown oil that crystallised on standing: $\delta_H$ (400 MHz, CDCl$_3$) 1.36 (12H, s), 7.32-7.37 (1H, m), 7.43-7.54 (3H, m), 7.63-7.68 (1H, m), 7.88-7.90 (2H, m).

3-Bromo-8-fluoro-7-(1-hydroxy-1-methylethyl)imidazo [1,2-α]pyridine (0.10 g, 0.36 mmol) and 4-fluoro-3'-(4,4,5, 5-tetramethyl-[1,3,2]dioxaborolan-2-yl)biphenyl-2-carbonitrile (0.15 g, 0.47 mmol) were coupled following the procedure in Example 1 to afford 4-fluoro-3'-[8-fluoro-7-(1-hydroxy-1-methylethyl)imidazo[1,2-α]pyridin-3-yl]biphenyl-2-carbonitrile as a white amorphous solid (75 mg, 53%): $\delta_H$ (360 MHz, CDCl$_3$) 1.74 (6H, s), 2.09 (1H, s), 7.19 (1H, dd, J 7 and 7), 7.30 (1H, ddd, J 8, 8 and 3), 7.49-7.58 (3H, m), 7.64-7.66 (2H, m), 7.73-7.75 (2H, m), 8.33 (1H, d, J 7); m/z (ES$^+$) 390 (M$^+$+H).

EXAMPLE 12

4,2'-Difluoro-5'-(8-fluoroimidazo[1,2α]-pyridin-3-yl)biphenyl-2-carbonitrile

5'-Bromo-4,2'-difluorobiphenyl-2-carbonitrile was converted to 4,2'-difluoro-5'-(5,5-dimethyl-[1,3,2]dioxaborinan-2-yl)biphenyl-2-carbonitrile using the procedure described in Example 2. This produced a brown oil that crystallised on standing: $\delta_H$ (360 MHz, CDCl$_3$) 1.03 (6H, s), 3.76 (4H, s), 7.20 (1H, dd, J 10 and 8), 7.33-7.38 (1H, m), 7.44-7.50 (2H, m), 7.81 (1H, dd, J 8 and 2), 7.85-7.90 (1H, m).

3-Bromo-8-fluoroimidazo[1,2-α]pyridine (0.10 g, 0.47 mmol) and 4,2'-difluoro-5'-(5,5-dimethyl-[1,3,2]dioxaborinan-2-yl)biphenyl-2-carbonitrile (0.28 g, 0.83 mmol) were coupled following the procedure in Example 1 to afford 4,2'-difluoro-5'-(8-fluoroimidazo[1,2-α]pyridin-3-yl)biphenyl-2-carbonitrile as a white amorphous solid (90 mg, 55%): $\delta_H$ (360 MHz, CDCl$_3$) 6.79-6.83 (1H, m), 6.94 (1H, dd, J 8 and 8), 7.73-7.46 (2H, m), 7.53-7.65 (4H, m), 7.73 (1H, s), 8.25 (1H, d, J 7); m/z (ES$^+$) 350 (M$^+$+H).

EXAMPLE 13

5'-(7-Chloro-8-fluoroimidazo[1,2-α]pyridin-3-yl)-4,2'-difluorobiphenyl-2-carbonitrile 3-Bromo-7-chloro-8-fluoroimidazo[1,2-α]pyridine (45 mg, 0.18 mmol) was coupled with 4,2'-difluoro-5'-(5,5-dimethyl-[1,3,2]dioxaborinan-2-yl)biphenyl-2-carbonitrile (49 mg, 0.19 mmol), as described in Example 1, to afford 5'-(7-chloro-8-fluoroimidazo[1,2-α]pyridin-3-yl)-4,2'-difluorobiphenyl-2-carbonitrile as a white amorphous solid (49 mg, 71%): $\delta_H$ (360 MHz, CDCl$_3$) 6.86 (1H, dd, J 7 and 7), 7.35-7.44 (2H, m), 7.58-7.64 (4H, m), 7.71 (1H, s), 8.20 (1H, d, J 7); m/z (ES$^+$) 384 (100%, [MH]$^+$).

EXAMPLE 14

3-(2'-Cyano-2,4'-difluorobiphenyl-5-yl)-8-fluoroimidazo[1, 2-α]pyridine-7-carboxylic acid methyl ester A mixture of lithium diisopropylamide (2M in heptane/tetrahydrofuran/ethylbenzene—stabilised with magnesium bis-(diisopropylamide), 16.7 ml) and tetrahydrofuran (30 ml) was cooled to −78° C. and a pre-cooled (−78° C.) solution of 2-chloro-3-fluoropyridine (4.0 g, 30.4 mmol) in tetrahydrofuran (30 ml) was added dropwise over 20 min. After 3 h, carbon dioxide was bubbled through the cold reaction mixture for 20 min. The reaction was then warmed to −30° C. for 1 h then warmed to 0° C. The mixture was quenched by the addition of water (75 ml). The aqueous phase was washed with diethyl ether (100 ml), then the pH of the solution adjusted to 2 by the addition of 2N hydrochloric acid. The resulting white precipitate was aged for 18 h then filtered and left to air-dry, which afforded 2-chloro-3-fluoroisonicotinic acid as a white solid (4.22 g, 79%): $\delta_H$ (360 MB, DMSO) 7.80 (1H, dd, J 5 and 5), 8.39 (1H, d, J 5), 14.20 (1H, s).

2-Chloro-3-fluoroisonicotinic acid (3.30 g, 18.8 mmol) was suspended in thionyl chloride (40 ml) and heated under reflux for 2.5 h. The solvent was evaporated and the residue dried by means of azeotropic removal of water with toluene (100 ml) to afford a pale yellow oil. The oil was dissolved in dichloromethane (20 ml) and cooled to 0° C. before methanol (2.42 g, 75.3 mmol) was added dropwise to the solution over 15 min. On complete addition the mixture was allowed to warm to ambient temperature and stirred for 18 h. The solvent was evaporated and the mixture partitioned between water (75 ml) and dichloromethane (100 ml). The aqueous phase was extracted further with dichloromethane (100 ml), the organic layers were combined, washed with brine (75 ml), dried over anhydrous sodium sulphate, filtered and evaporated to give 2-chloro-3-fluoroisonicotinic acid methyl ester (3.32 g, 93%) as a pale yellow solid: $\delta_H$ (360 MHz, CDCl$_3$) 3.99 (3H, s), 7.70 (1H, dd, J 5 and 5), 8.31 (1H, d, J 5).

2-Chloro-3-fluoroisonicotinic acid methyl ester (3.32 g, 17.5 mmol) was converted to 8-fluoroimidazo[1,2-α]pyridine-7-carboxylic acid methyl ester (1.4 g, 41%) as described in Example 1.

8-Fluoroimidazo[1,2-α]pyridine-7-carboxylic acid methyl ester (0.19 g, 1.0 mmol) was brominated as described in Example 1, affording 3-bromo-8-fluoroimidazo[1,2-α] pyridine-7-carboxylic acid methyl ester (195 mg, 71%): $\delta_H$ (360 MHz, CDCl$_3$) 4.00 (3H, s), 7.32 (1H, t, J 6.9), 7.43 (1H, dd, J 7 and 6), 8.19 (1H, s), 8.37 (1H, d, J 7).

3-Bromo-8-fluoroimidazo[1,2-α]pyridine-7-carboxylic acid methyl ester (0.10 g, 0.37 mmol) and 4,2'-difluoro-5'-(5,5-dimethyl-[1,3,2]dioxaborinan-2-yl)biphenyl-2-carbonitrile (0.15 g, 0.44 mmol) were coupled following the procedure in Example 1 to afford 3-(2'-cyano-2,4'-difluorobiphenyl-5-yl)-8-fluoroimidazo[1,2-α]pyridine-7-carboxylic acid methyl ester (79 mg, 53%) as a white solid: $\delta_H$ (400 MHz, CDCl$_3$) 4.00 (3H, s), 7.35 (1H, dd, J 7 and 7), 7.34-7.46 (2H, m), 7.53-7.66 (4H, m), 7.85 (1H, s), 8.24 (1H, d, J 7); m/z (ES$^+$) 408 (100%, [MH]$^+$).

EXAMPLE 15

4,2'-Difluoro-5'-[8-fluoro-7-(1-fluoro-1-methylethyl)imidazo[1,2-α]pyridin-3-yl]biphenyl-2-carbonitrile 4,2'-Difluoro-5'-[8-fluoro-7-(1-hydroxy-1-methylethyl) imidazo[1,2-α]pyridin-3-yl]biphenyl-2-carbonitrile (0.10 g, 0.245 mmol) was dissolved in 70% HF/pyridine (2 ml) and dichloromethane (1 ml) and left to stir at room temperature for 18 h. The mixture was slowly added to water and then extracted with ethyl acetate (75 ml). The organic layer was washed with water (50 ml) and brine (50 ml), dried over anhydrous sodium sulphate and evaporated to give a colourless oil. The oil was purified by silica cartridge eluting with dichloromethane. Collecting appropriate fractions followed by evaporation gave a white solid. The solid was further purified by preparative HPLC chromatography eluting with an isocratic system (40% MeCN/60% H$_2$O+0.1% TFA). Collecting appropriate fractions, evaporation and trituration with diethyl ether gave 4,2'-difluoro-5'-[8-fluoro-7-(1-fluoro-1-methylethyl)imidazo[1,2-α]pyridin-3-yl]biphenyl- 2-carbonitrile (31 mg, 31%) as a white solid: $\delta_H$ (500 MHz, CDCl$_3$) 1.83 (6H, d, J 23), 7.06 (1H, dd, J 7 and 7), 7.38-7.45 (2H, m), 7.54 (1H, dd, J 8 and 3), 7.57-7.64 (3H, m), 7.72 (1H, s), 8.24 (1H, d, J 7); m/z (ES$^+$) 410 (100%, [MH]$^+$).

EXAMPLE 16

4'-Fluoro-3'-[8-fluoro-7-(1-hydroxy-1-methylethyl)imidazo[1,2-α]pyridin-3-yl]biphenyl-2-carbonitrile 2-(3-Bromo-8-fluoroimidazo[1,2-α]pyridin-7-yl)propan-2-ol was coupled to 4'-fluoro-3'-(4,4,5,5-tetramethyl-[1,3,2]dioxaborolan-2-yl)-biphenyl-2-carbonitrile (prepared as described in WO 02/074773) as described in Example 1 to give 4'-fluoro-3'-[8-fluoro-7-(1-hydroxy-1-methylethyl)imidazo[1,2-α]pyridin-3-yl]biphenyl-2-carbonitrile as an off-white solid (217 mg, 56%): $\delta_H$ (360 MHz, CDCl$_3$) 1.74 (6H, s), 2.15 (1H, s), 7.22 (1H, t, J 7), 7.40 (1H, t, J 9), 7.48-7.73 (5H, m), 7.79-7.81 (2H, m), 8.06 (1H, dd, J 7 and 2); m/z (ES$^+$) 390 [MH$^+$].

EXAMPLE 17

3'-Fluoro-5'-[8-fluoro-7-(1-hydroxy-1-methylethyl)imidazo[1,2-α]pyridin-3-yl]biphenyl-2-carbonitrile 2-(3-Bromo-8-fluoroimidazo[1,2-α]pyridin-7-yl)propan-2-ol was coupled to 3'-fluoro-5'-(4,4,5,5-tetramethyl-[1,3,2]dioxaborolan-2-yl)biphenyl-2-carbonitrile (prepared as described in WO 02/074773) as described in Example 1 to give 3'-fluoro-5'-[8-fluoro-7-(1-hydroxy-1-methylethyl)imidazo[1,2-α]pyridin-3-yl]biphenyl-2-carbonitrile as an off-white solid (200 mg, 51%): $\delta_H$ (360 MHz, CDCl$_3$) 1.74 (6H, s), 2.13 (1H, s), 7.24 (1H, s), 7.27-7.29 (1H, m), 7.34-7.37 (1H, m), 7.51-7.58 (3H, m), 7.69-7.73 (1H, m), 7.76 (1H, s), 7.84 (1H, dd, J 8 and 1), 8.39 (1H, d, J 7); m/z (ES$^+$) 390 [MH$^+$].

EXAMPLE 18

2-{3-[3-(3,5-Difluoropyridin-4-yl)-4-fluorophenyl]-8-fluoroimidazo[1,2-α]pyridin-7-yl}propan-2-ol 3-(3,5-Difluoropyridin-4-yl)-4-fluorophenylamine was bromo-deaminated, following the procedure in Example 2, to give 4-(5-bromo-2-fluorophenyl)-3,5-difluoropyridine as a yellow solid (180 mg, 54%): $\delta_H$ (360 MHz, CDCl$_3$) 7.14 (1H, t, J 9), 7.55 (1H, dd, J 6 and 2), 7.58-7.63 (1H, m), 8.47 (2H, s).

2-(8-Fluoroimidazo[1,2-α]pyridin-7-yl)propan-2-ol was coupled to 4-(5-bromo-2-fluorophenyl)-3,5-difluoropyridine as described in Example 6 to give 2-{3-[3-(3,5-difluoropyridin-4-yl)-4-fluorophenyl]-8-fluoroimidazo[1,2-α]pyridin-7-yl}propan-2-ol as an off-white solid (80 mg, 40%): $\delta_H$ (360 MHz, d$_6$-DMSO) 1.57 (6H, s), 7.22 (1H, t, J 7), 7.66 (1H, t, J 9), 7.83 (1H, s), 7.94 (2H, dd, J 6 and 2), 8.37 (1H, d, J 7), 8.75 (2H, s); m/z (ES$^+$) 402 [MH$^+$].

EXAMPLE 19

5,2'-Difluoro-5'-[8-fluoro-7-(1-hydroxy-1-methylethyl)imidazo[1,2-α]pyridin-3-yl]biphenyl-2-carbonitrile 2-(8-Fluoroimidazo[1,2-α]pyridin-7-yl)propan-2-ol was coupled to 5'-bromo-5,2'-difluorobiphenyl-2-carbonitrile (prepared as described in WO 02/38568) as described in Example 6 to give 5,2'-difluoro-5'-[8-fluoro-7-(1-hydroxy-1-methylethyl)imidazo[1,2-α]pyridin-3-yl]biphenyl-2-carbonitrile as a white solid (90 mg, 43%): $\delta_H$ (360 MHz, d$_6$-DMSO) 1.58 (6H, s), 7.21 (1H, m), 7.54-7.65 (2H, m), 7.77 (1H, dd, J 10 and 3), 7.84-7.89 (3H, m), 8.15 (1H, dd, J 9 and 6), 8.49 (1H, d, J 7); m/z (ES$^+$) 408 [MH$^+$].

EXAMPLE 20

2'-Fluoro-3'-[8-fluoro-7-(1-hydroxy-1-methylethyl)imidazo[1,2-α]pyridin-3-yl]biphenyl-2-carbonitrile 2-(3-Bromo-8-fluoroimidazo[1,2-α]pyridin-7-yl)propan-2-ol was coupled to 2'-cyano-2-fluorobiphenyl-3-boronic acid (prepared as described in WO 02/38568) as described in Example 1 to give 2'-fluoro-3'-[8-fluoro-7-(1-hydroxy-1-methylethyl)imidazo[1,2-α]pyridin-3-yl]biphenyl-2-carbonitrile as an off-white solid (55 mg, 30%): $\delta_H$ (360 MHz, CDCl$_3$) 2.36 (6H, d, J 1), 7.83 (1H, t, J 7), 8.03-8.26 (5H, m), 8.32-8.36 (1H, m), 8.39 (1H, s), 8.44 (1H, d, J 8), 8.69 (1H, q, J 4); m/z (ES$^+$) 390 [MH$^+$].

EXAMPLE 21

3'-[8-Fluoro-7-(1-hydroxy-1-methylethyl)imidazo[1,2-α]pyridin-3-yl]-6,2',6'-trifluorobiphenyl-2-carbonitrile 3-Bromo-2,4-difluorophenylamine and 3-fluoro-2-(4,4,5,5-tetramethyl-[1,3,2]dioxaborolan-2-yl)benzonitrile were coupled together as described in Example 2 to give 3'-amino-6,2',6'-trifluorobiphenyl-2-carbonitrile as an off-white solid (400 mg, 25%): $\delta_H$ (360 MHz, CDCl$_3$) 6.88 (2H, s), 7.41-7.46 (1H, m), 7.50-7.56 (1H, m), 7.61 (1H, dd, J 7 and 1).

3'-Amino-6,2',6'-trifluorobiphenyl-2-carbonitrile was converted to 3'-bromo-6,2',6'-trifluorobiphenyl-2-carbonitrile, as described in Example 2, to give a pale yellow solid (150 mg, 30%): $\delta_H$ (360 MHz, CDCl$_3$) 6.99-7.04 (1H, m), 7.44-7.49 (1H, m), 7.55-7.72 (3H, m).

2-(8-Fluoroimidazo[1,2-α]pyridin-7-yl)propan-2-ol was coupled to 3'-bromo-6,2',6'-trifluorobiphenyl-2-carbonitrile as described in Example 6 to give 3'-[8-fluoro-7-(1-hydroxy-1-methylethyl)imidazo[1,2-α]pyridin-3-yl]-6,2',6'-trifluorobiphenyl-2-carbonitrile as an off-white solid (17 mg, 10%): $\delta_H$ (400 MHz, d$_6$-DMSO) 1.58 (6H, s), 5.56 (1H, s), 7.23 (1H, t, J 7), 7.61 (1H, t, J 8), 7.84-7.87 (3H, m), 7.95-8.01 (2H, m), 8.08 (1H, dd, J 7 and 3); m/z (ES$^+$) 426 [MH$^+$]

EXAMPLE 22

4,4'-Difluoro-3'-[8-fluoro-7-(1-hydroxy-1-methylethyl)imidazo[1,2-α]pyridin-3-yl]biphenyl-2-carbonitrile 2-(8-Fluoroimidazo[1,2-α]pyridin-7-yl)propan-2-ol was coupled to 3'-bromo-4,4'-difluorobiphenyl-2-carbonitrile (prepared in the same way as in Example 2) as described in Example 6 to give 4,4'-difluoro-3'-[8-fluoro-7-(1-hydroxy-1-methylethyl)imidazo[1,2-α]pyridin-3-yl]biphenyl-2-carbonitrile (trifluoroacetate salt) as an off-white solid (23 mg, 6%); m/z (ES$^+$) 408 [MH$^+$].

EXAMPLE 23

3-Chloro-2'-fluoro-5'-[8-fluoro-7-(1-hydroxy-1-methylethyl)imidazo[1,2-α]pyridin-3-yl]biphenyl-4-carbonitrile 5'-Bromo-3-chloro-2'-fluorobiphenyl-4carbonitrile (2.2 g, 66%) was prepared in the same way as in Example 2 (3.0 g, 99%): $\delta_H$ (360 MHz, CDCl$_3$) 7.09 (1H, dd, J 7 and 6), 7.09 (1H, m), 7.49-7.52 (3H, m), 7.68 (1H, s), 7.75-7.76 (1H, m).

2-(8-Fluoroimidazo[1,2-α]pyridin-7-yl)propan-2-ol and 5'-bromo-3-chloro-2'-fluorobiphenyl-4-carbonitrile were coupled in the same way as in Example 6 to give 3-chloro-2'-fluoro-5'-[8-fluoro-7-(1-hydroxy-1-methylethyl)imidazo[1,2-α]pyridin-3-yl]biphenyl-4-carbonitrile as an off-white solid (20 mg, 7%): $\delta_H$ (400 MHz, d$_6$-DMSO) 1.59 (6H, s), 7.33 (1H, t, J 7), 7.63 (1H, dd, J 11 and 9), 7.80-7.89 (2H, m), 7.96 (1H, dd, J 7 and 2), 8.03 (1H, s), 8.11-8.14 (2H, m), 8.53 (1H, d, J 7); m/z (ES$^+$) 424 [MH$^+$].

EXAMPLE 24

1-{2-Fluoro-5-[8-fluoro-7-(1-hydroxy-1-methylethyl)imidazo[1,2-α]pyridin-3-yl]phenyl}pyrrolidin-2-one A solution of 5-bromo-2-fluoroaniline (10 g, 52 mmol) in toluene (150 ml) was treated with 4-bromobutyryl chloride (6.1 ml, 52 mmol) and then heated at 100° C. for 14 h. The reaction was cooled then washed with water, 10% sodium carbonate, 1N HCl and water, dried over anhydrous magnesium sulphate, filtered and concentrated in vacuo. The resulting tan solid was triturated with 5% ether in isohexane and collected by filtration to afford 4-bromo-N-(5-bromo-2-fluorophenyl)butyramide. This solid was dissolved in anhydrous N,N-dimethylformamide (150 ml) then treated with sodium hydride (1.4 g of a 60% dispersion in oil) added in portions over 5 min. The resulting mixture was stirred at 60° C. for 60 min, cooled and treated with methanol (10 ml). The reaction was diluted with water (1500 ml) and extracted with ether (2×400 ml). The organics were combined, washed with water (×3), brine, dried over anhydrous magnesium sulphate, filtered and pre-adsorbed onto silica. Chromatography on silica gel, eluting with isohexane on a gradient of ethyl acetate (20-50%), gave 1-(5-bromo-2-fluorophenyl)pyrrolidin-2-one (9.1 g, 67%) as a straw-coloured solid: $\delta_H$ (400 MHz, CDCl$_3$) 2.17-2.25 (2H, m), 2.55-2.59 (2H, m), 3.80-3.84 (2H, m), 7.20 (1H, dd, J 10.5 and 9), 7.33-7.37 (1H, m), 7.59 (1H, dd, J 7 and 2.5).

2-(8-Fluoroimidazo[1,2-α]pyridin-7-yl)propan-2-ol was coupled to 1-(5-bromo-2-fluorophenyl)pyrrolidin-2-one as described in Example 6 to give 1-{2-fluoro-5-[8-fluoro-7-(1-hydroxy-1-methylethyl)imidazo[1,2-α]pyridin-3-yl]phenyl}pyrrolidin-2-one as a pale yellow solid (114 mg, 31%): m/z (ES$^+$) 372 [MH$^+$].

EXAMPLE 25

2-{8-Fluoro-3[-4-fluoro-3-(imidazol-1-yl)phenyl]imidazo[1,2-α]pyridin-7-yl}propan-2-ol 2-(8-Fluoroimidazo[1,2-α]pyridin-7-yl)propan-2-ol was coupled to 1-(5-bromo-2-fluorophenyl)-1H-imidazole as described in Example 6 to give 2-{8-fluoro-3-[4-fluoro-(3-imidazol-1-yl)phenyl]imidazo[1,2-α]pyridin-7-yl}propan-2-ol as a pale yellow solid (83 mg, 24%): m/z (ES$^+$) 355 [MH$^+$].

EXAMPLE 26

4,3'-Difluoro-5'-[8-fluoro-7-(1-hydroxy-1-methylethyl)imidazo[1,2-α]pyridin-3-yl]biphenyl-2-carbonitrile A suspension of 2-bromo-5-fluorobenzonitrile (30.0 g, 150 mmol), bis(pinacolato)diboron (41.9 g, 165 mmol) and potassium acetate (29.4 g, 300 mmol) in 1,4-dioxane (375 ml) and DMSO (30 ml) was degassed with nitrogen for 1 h. Dichloro[1,1'-bis(diphenylphosphino)ferrocene]-palladium (II) dichloromethane adduct (3.7 g, 4.5 mmol) was added and the mixture heated at 90° C. for 18 h. The mixture was allowed to cool to ambient temperature then diluted with diethyl ether (300 ml) and filtered through a glass microfibre filter paper. The solvent was evaporated and the residue was treated with ice-cold 2N sodium hydroxide solution (250 ml) and the mixture left to stir for 15 min. The aqueous phase was extracted with diethyl ether (200 ml). The pH of the aqueous was adjusted to 5 by the addition of concentrated hydrochloric acid. The aqueous phase was extracted with diethyl ether (2×200 ml), the organic phase was combined, washed with water (150 ml) and brine (150 ml), dried over anhydrous sodium sulphate, filtered and evaporated to give 5-fluoro-2-(4,4,5,5-tetramethyl-[1,3,2]dioxaborolan-2-yl)benzonitrile (36.5 g, 98%) as a brown oil which crystallised on standing: $\delta_H$ (360 MHz, CDCl$_3$) 1.38 (12H, s), 7.25-7.30 (1H, m), 7.40 (1H, dd, J 3 and 8), 7.91 (1H, dd, J 6 and 8).

5-Fluoro-2-(4,4,5,5-tetramethyl-[1,3,2]dioxaborolan-2-yl)-benzonitrile (0.99 g, 4.0 mmol) and 1,3-dibromo-5-fluorobenzene (1.52 g, 6.0 mmol) were suspended in 1,2-dimethoxyethane (8 ml) and 2N sodium carbonate solution (4 ml) and degassed for 30 min before addition of tetrakis(triphenylphosphine)palladium(0). On complete addition the mixture was heated at 65° C. for 20 h. The mixture was partitioned between ethyl acetate (100 ml) and water (50 ml), the organic layer separated and washed with brine (50 ml), dried over anhydrous sodium sulphate, filtered and evaporated onto silica. The product was purified by flash column chromatography on silica, eluting with isohexane on a gradient of diethyl ether (5-100%). Combination of the desired fractions and evaporation gave 3'-bromo-4,5'-difluorobiphenyl-2-carbonitrile (110 mg, 9%) as a white solid: $\delta_H$ (500 Mfz, CDCl$_3$) 7.53-7.55 (1H, m), 7.67 (1H, s), 7.69-7.76 (3H, m), 8.03 (1H, dd, J 9 and 2).

2-(8-Fluoroimidazo[1,2-α]pyridin-7-yl)propan-2-ol (58 mg, 0.3 mmol) and 3'-bromo-4,5'-difluorobiphenyl-2-carbonitrile (106 mg, 0.36 mmol) were coupled following the procedure in Example 6 to afford 4,3'-difluoro-5'-[8-fluoro-7-(1-hydroxy-1-methylethyl)imidazo[1,2-α]pyridin-3-yl]-biphenyl-2-carbonitrile (25 mg, 20%) as a white solid: $\delta_H$ (500 Ndz, CDCl$_3$) 1.74 (6H, s), 2.07 (1H, s), 7.22-7.26 (2H, m), 7.35 (1H, d, J 9), 7.39-7.45 (1H, m), 7.51-7.57 (3H, m), 7.76 (1H, s), 8.35 (1H, d, J 7); m/z (ES$^+$) 408 (100%, [MH]$^+$).

EXAMPLE 27

3'-[8-Fluoro-7-(1-hydroxy-1-methylethyl)imidazo[1,2-α]pyridin-3-yl]-4,2',6'-trifluorobiphenyl-2-carbonitrile A suspension of 2-bromo-5-fluorobenzonitrile (10.0 g, 50 mmol), potassium fluoride (9.59 g, 165 mmol) and 2,6-difluorophenylboronic acid (9.87 g, 62.5 mmol) in tetrahydrofuran (120 ml) and water (15 ml) was degassed with nitrogen for 30 min. Tris(dibenzylidineacetone)-dipalladium (0) (916 mg, 1.0 mmol) and tri-tert-butylphosphine (10% w/w solution in hexane, 0.5 ml) were added and the mixture stirred at ambient temperature for 18 h. The black solution was washed with 1N sodium hydroxide solution (2×100 ml), and the aqueous phase was re-extracted with diethyl ether (100 ml). The combined organic layer was washed with brine (50 ml), filtered through a glass microfibre filter paper then evaporated to give an orange solid. The solid was suspended in 2-propanol (120 ml) and heated to 70° C. to aid dissolution. The solution was left to cool to ambient temperature then water (120 ml) added dropwise over 1 h. The solid was filtered and washed with 2-propanol/water (1:1, 30 ml) then dried under vacuum to give 4,2',6'-trifluorobiphenyl-2-carbonitrile (9.92 g, 85%) as a grey solid: $\delta_H$ (360 MHz, CDCl$_3$) 7.06 (2H, t, J 8), 7.38-7.52 (4H, m).

To a slurry of 4,2',6'-trifluorobiphenyl-2-carbonitrile (5.0 g, 21.4 mmol) and 1,3-dibromo-5,5-dimethylhydantoin (3.37 g, 11.8 mmol) in acetonitrile (45 ml) was added concentrated sulphuric acid (3.15 g, 32.2 mmol). The slurry was warmed to 70° C. and the resulting solution stirred for 7 h then stood at ambient temperature for 18 h. Water (45 ml) was added dropwise to the solution over 15 min. The layers were allowed to settle and the product rapidly crystallised. The slurry was left to stir for 0.5 h then filtered, washed with 1:1 acetonitrile/water (10 ml) and left to air-dry, which gave 3'-bromo-4,2',6'-trifluorobiphenyl-2-carbonitrile (6.3 g, 94%) as a white solid: $\delta_H$ (360 I, CDCl$_3$) 6.97-7.08 (1H, m), 7.38-7.54 (2H, m), 7.62-7.68 (1H, m).

2-(8-Fluoroimidazo[1,2-α]pyridin-7-yl)propan-2-ol (194 mg, 1.0 mmol) and 3'-bromo-4,2',6'-trifluorobiphenyl-2-carbonitrile (343 mg, 1.1 mmol) were coupled following the procedure in Example 6 to afford 3'-[8-fluoro-7-(1-hydroxy-1-methylethyl)imidazo[1,2-α]pyridin-3-yl]-4,2',6'-trifluorobiphenyl-2-carbonitrile (155 mg, 36%) as a white solid: $\delta_H$ (360 MHz, CDCl$_3$) 1.74 (6H, s), 2.07 (1H, s), 7.19-7.26 (2H, m), 7.41-7.49 (1H, m), 7.54-7.65 (3H, m), 7.73 (1H, s), 7.93 (1H, dd, J 7 and 7); m/z (ES$^+$) 426 (100%, [MH]$^+$).

EXAMPLE 28

2-{8-Fluoro-3-[4-fluoro-3-(1-methyl-1H-[1,2,3]triazol-4-ylmethoxy)phenyl]-imidazo[1,2-α]pyridin-7-yl}propan-2-ol A cooled (–20° C.) solution of 2,2,6,6-tetramethylpiperidine (28 ml, 165 mmol) in tetrahydrofuran (400 ml) was treated with m-butyllithium (63 ml of a 2.5M solution in hexanes, 157.5 mmol). This mixture was then cooled to –78° C. 1-Bromo-4-fluorobenzene (16.5 ml, 150 mmol) was then added neat and dropwise over 10 min and stirring at –78° C. was continued for 3 h. Triisopropyl borate (40 ml, 172.5 mmol) was then added and stirring at –78° C. continued for 30 min before removing the cooling bath. When the internal temperature of the reaction reached –4° C., 5N hydrochloric acid (75 ml) was added and the mixture was stirred to ambient temperature. After stirring at ambient temp for 1 h the majority of the tetrahydrofuran was removed and the mixture partitioned between ether (500 ml) and 1N hydrochloric acid (500 ml). The organics were then extracted with 2N sodium hydroxide (400 ml) and the organics were discarded. The aqueous was cooled in an ice-water bath and 5N hydrochloric acid (150 ml) was added dropwise over 15 min. The resulting white solid was collected and dried under vacuum to afford 5-bromo-2-fluorobenzeneboronic acid (25 g, 76%).

A solution of 5-bromo-2-fluorobenzeneboronic acid (25 g, 114 mmol) in tetrahydrofuran was treated with hydrogen peroxide (7.8 ml of a 35 wt % solution in water) then with sodium hydroxide (1.4 ml of a 4N solution in water). A mild exotherm caused the internal temperature to reach 40° C. This mixture was left to stir at ambient temperature for 14 h then treated with manganese dioxide (200 mg) and stirring was continued for 90 min before filtering the reaction (GF/A filter paper). The filtrate was concentrated on a rotary evaporator and the residue partitioned between ether (400 ml) and water. The organics were washed with more water and brine, and dried over anhydrous magnesium sulphate. Filtration and evaporation to dryness afforded 5-bromo-2-fluorophenol (19.7 g, 90%) as a colourless liquid: $\delta_H$ (400 MHz, d$_6$-DMSO) 6.93-6.97 (1H, m), 7.09-7.14 (2H, m), 10.36 (1H, br).

An ice-cooled solution of 5-bromo-2-fluorophenol (1.91 g, 10 mmol), (1-methyl-1H-[1,2,3]triazol-4-yl)methanol (1.24 g, 11 mmol) and triphenylphosphine (3.93 g, 15 mmol) in tetrahydrofuran (50 ml) was treated dropwise with diisopropyl azodicarboxylate (3.03 g, 15 mmol) over 10 min. The resulting mixture was stirred to ambient temperature over 12 h and then glacial acetic acid (1 ml) was added. The reaction mixture was concentrated in vacuo then partitioned between ethyl acetate and 0.01N sodium hydroxide solution. The organics were washed with water, brine, dried over anhydrous magnesium sulphate and concentrated to give an oil. This oil was purified by chromatography on silica gel, eluting with isohexane on a gradient of ethyl acetate (20-50%). Product-containing fractions were concentrated and the resulting residue triturated with 10% ether in isohexane to furnish 4-(5-bromo-2-fluorophenoxymethyl)-1-methyl-1H-[1,2,3]triazole as a white solid (1.9 g, 66%): $\delta_H$ (360 MHz, d$_6$-DMSO) 4.06 (3H, s), 5.25 (2H, s), 7.10-7.20 (2H, m), 7.55-7.70 (1H, m), 8.19 (1H, s).

2-(8-Fluoroimidazo[1,2-α]pyridin-7-yl)propan-2-ol was coupled to 4-(5-bromo-2-fluorophenoxymethyl)-1-methyl-1H-[1,2,3]triazole as described in Example 6 to give 2-{8-fluoro-3-[4-fluoro-3-(1-methyl-1H-[1,2,3]triazol-4-ylmethoxy)phenyl]imidazo[1,2-α]pyridin-7-yl}propan-2-ol as an off-white solid: $\delta_H$ (400 MHz, d$_6$-DMSO) 1.58 (6H, s), 4.07 (3H, s), 5.35 (2H, s), 5.55 (1H, s), 7.16-7.23 (2H, m), 7.37 (1H, dd, J 11 and 9), 7.65 (1H, dd, J 8 and 2), 7.76 (1H, s), 8.21 (1H, s), 8.43 (1H, d, J 7); m/z (ES$^+$) 400 [MH$^+$].

EXAMPLE 29

3-(2,4'-Difluoro-2'-methanesulfonylbiphenyl-5-yl)-8-fluoro-7-(1-hydroxy-1-methylethyl)imidazo[1,2-α]pyridine To a solution of 1-bromo-4-fluoro-2-methylsulfanylbenzene in dichloromethane was added meta-chloroperbenzoic acid. After stirring overnight at room temperature, the reaction mixture was diluted with ethyl acetate and extracted with sodium sulphite solution and sodium bicarbonate solution. The organic layer was dried and concentrated. The resulting residue was purified by dry flash column chromatography on silica gel, eluting with isohexane on a gradient of ethyl acetate (0-50%), to give 1-bromo-4-fluoro-2-methanesulfonylbenzene as a white solid (9 g, 80%): $\delta_H$ (400 MHz, CDCl$_3$) 3.30 (3H, s), 7.20-7.24 (1H, m), 7.76 (1H, dd, J 9 and 5), 7.95 (1H, dd, J 8 and 3).

1-Bromo-4-fluoro-2-methanesulfonylbenzene was converted to 5'-bromo-4,2'-difluoro-2-methanesulfonylbiphenyl in the same way as in Example 2 to give a yellow oil (4.5 g, 72%): $\delta_H$ (360 MHz, CDCl$_3$) 2.90 (3H, s),7.05 (1H, t, J 9), 7.36-7.40 (2H, m), 7.49 (1H, dd, J 7 and 3), 7.52-7.57 (1H, m), 7.94 (1H, dd, J 8 and 3).

2-(8-Fluoroimidazo[1,2-α]pyridin-7-yl)propan-2-ol was coupled to 5'-bromo-4,2'-difluoro-2-methanesulfonylbiphenyl as described in Example 6 to give 3-(2,4'-difluoro-2'-methanesulfonylbiphenyl-5-yl)-8-fluoro-7-(1-hydroxy-1-methylethyl)imidazo[1,2-α]pyridine as an off-white solid (149 mg, 33%): $\delta_H$ (400 MHz, d$_6$-DMSO) 1.57 (6H, s), 3.11 (3H, s), 5.54 (1H, s), 7.20 (1H, t, J 7), 7.49 (1H, t, J 9), 7.65-7.79 (5H, m), 7.96 (1H, dd, J 9 and 3), 8.40 (1H, d, J 7); m/z (ES$^+$) 461 [MH$^+$].

EXAMPLE 30

1-{2'-Fluoro-5'-[8-fluoro-7-(1-hydroxy-1-methylethyl)imidazo[1,2-α]pyridin-3-yl]biphenyl-4-yl}ethanone 2-(3-Bromo-8-fluoroimidazo[1,2-α]pyridin-7-yl)propan-2-ol and 3-chloro-4-fluorobenzeneboronic acid were coupled together as described in Example 1 to give 2-[3-(3-chloro-4-fluorophenyl)-8-fluoroimidazo[1,2-α]pyridin-7-yl]propan-2-ol as a white solid (7.10 g, 85%): $\delta_H$ (400 MHz, CDCl$_3$) 1.74 (6H, s), 2.08 (1H, s), 7.21 (1H, t, J 7), 7.31 (1H, t, J 9), 7.40-7.44 (1H, m), 7.60 (1H, dd, J 7 and 2), 7.67 (1H, s), 8.01 (1H, d, J 7); m/z (ES$^+$) 323 [MH$^+$].

2-[3-(3-Chloro-4-fluorophenyl)-8-fluoroimidazo[1,2-α]pyridin-7-yl]-propan-2-ol, 4acetylbenzeneboronic acid and potassium phosphate were placed in a dry tube with 1,4dioxane/water (3:1) and this was heated to 70° C. under nitrogen. Tris(dibenzylideneacetone)dipalladium(0), tri-tert-butylphosphine (0.2M in 1,4dioxane) and 1,4-dioxane (0.5 ml) were mixed in a vial, and this mixture was added to the hot reaction via syringe. The resulting reaction mixture was heated at 70° C. for 12 h. The reaction was allowed to cool to room temperature then partitioned between dichloromethane and 2N hydrochloric acid. The aqueous layer was filtered through glass microfibre filter paper and evaporated to dryness. The residue was dissolved in methanol and evaporated to dryness. The residue was dissolved in dimethylsulfoxide (~25 mg/ml), filtered through glass microfibre filter paper and purified by LC-MS. Appropriate fractions were combined and evaporated to give 1-{2'-fluoro-5'-[8-fluoro-7-(1-hydroxy-1-methylethyl)imidazo[1,2-α]pyridin-3-yl]biphenyl-4-yl}ethanone as an off-white solid (6 mg, 5%); m/z (ES$^+$) 407 [MH$^+$].

EXAMPLE 31

2-[3-(2,4'-Difluoro-2'-methylbiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol (100 mg, 0.36 mmol) and 4-fluoro-2-methylphenylboronic acid (83 mg, 0.54 mmol) were coupled using the procedure in Example 30 to afford 2-[3-(2,4'-difluoro-2'-methylbiphenyl-5-yl)-8-fluoroimidazo[1,2-α]pyridin-7-yl]propan-2-ol (83 mg, 58%) as a white solid: $\delta_H$ (360 MHz, CDCl$_3$) 1.74 (6H, s), 2.04 (1H, s), 2.26 (3H, s), 6.95-7.05 (2H, m), 7.15-7.33 (3H, m), 7.40 (1H, dd, J 7 and 2), 7.51-7.56 (1H, m), 7.69 (1H, s), 8.06 (1H, d, J 7); m/z (ES$^+$) 397 (100%, [MH]$^+$).

EXAMPLE 32

2'-Fluoro-5'-[8-fluoro-7-(1-hydroxy-1-methylethyl)imidazo[1,2-αα]pyridin-3-yl]biphenyl-3-carbonitrile 2-[3-(3-Chloro-4-fluorophenyl)-8-fluoroimidazo[1,2-α]pyridin-7-yl]-propan-2-ol (100 mg, 0.36 mmol) and 3-cyanophenylboronic acid (79 mg, 0.54 mmol) were coupled using the procedure in Example 30 to afford 2'-fluoro-5'-[8-fluoro-7-(1-hydroxy-1-methylethyl)imidazo[1,2-α]pyridin-3-yl]biphenyl-3-carbonitrile (112 mg, 80%) as a white solid: $\delta_H$ (360 MHz, CDCl$_3$) 1.74 (6H, s), 2.02 (1H, s), 7.20 (1H, dd, J 7 and 7), 7.37 (1H, dd, J 9 and 9), 7.54-7.63 (3H, m), 7.70-7.73 (2H, m), 7.82 (1H, d, J 9), 7.89 (1H, s), 8.04 (1H, d, J 7); m/z (ES$^+$) 390 (100%, [MH]$^+$).

EXAMPLE 33

1-{2'-Fluoro-5'-[8-fluoro-7-(1-hydroxy-1-methylethyl)imidazo[1,2-α]pyridin-3-yl]biphenyl-3-yl}ethanone 2-[3-(3-Chloro-4-fluorophenyl)-8-fluoroimidazo[1,2-α]pyridin-7-yl]-propan-2-ol and 3-acetylbenzeneboronic acid were coupled in the same way as in Example 30 to give 1-{2'-fluoro-5'-[8-fluoro-7-(1-hydroxy-1-methylethyl)imidazo[1,2-α]pyridin-3-yl]biphenyl-3-yl}ethanone as an off-white solid (14 mg, 11%): m/z (ES$^+$) 407 [MH$^+$].

EXAMPLE 34

2-[8-Fluoro-3-(2-fluoro-5'-isopropyl-2'-methoxybiphenyl-5-yl)imidazo[1,2-α]pyridin-7-yl]propan-2-ol 2-[3-(3-Chloro-4-fluorophenyl)-8-fluoroimidazo[1,2-α]pyridin-7-yl]-propan-2-ol and 5-isopropyl-2-methoxybenzeneboronic acid were coupled in the same way as in Example 30 to give 2-[8-fluoro-3-(2-fluoro-5'-isopropyl-2'-methoxybiphenyl-5-yl)imidazo[1,2-α]pyridin-7-yl]propan-2-ol as an off-white solid (8 mg, 6%): m/z (ES$^+$) 437 [MH$^+$].

EXAMPLE 35

2'-Fluoro-5'-[8-fluoro-7-(1-hydroxy-1-methylethyl)imidazo[1,2-α]pyridin-3-yl]biphenyl-4-carbaldehyde 2-[3-(3-Chloro-4-fluorophenyl)-8-fluoroimidazo[1,2-α]pyridin-7-yl]-propan-2-ol and 4-formylbenzeneboronic acid were coupled in the same way as in Example 30 to give 2'-fluoro-5'-[8-fluoro-7-(1-hydroxy-1-methylethyl)imidazo[1,2-α]pyridin-3-yl]biphenyl-4-carbaldehyde as an off-white solid (100 mg, 83%): m/z (ES$^+$) 393 [MH$^+$].

EXAMPLE 36

2-[8-Fluoro-3-(2-fluoro-4'-trifluoromethylbiphenyl-5-yl)imidazo[1,2-α]pyridin-7-yl]propan-2-ol 2-[3-(3-Chloro-4-fluorophenyl)-8-fluoroimidazo[1,2-α]pyridin-7-yl]-propan-2-ol and 4-trifluoromethylbenzeneboronic acid were coupled in the same way as in Example 30 to give 2-[8-fluoro-3-(2-fluoro-4'-trifluoromethylbiphenyl-5-yl)imidazo[1,2-α]pyridin-7-yl]propan-2-ol as an off-white solid (10 mg, 7%): m/z (ES$^+$) 433 [MH$^+$].

EXAMPLE 37

2'-Fluoro-5'-[8-fluoro-7-(1-hydroxy-1-methylethyl)imidazo[1,2-α]pyridin-3-yl]biphenyl-4-carbonitrile 2-[3-(3-Chloro-4-fluorophenyl)-8-fluoroimidazo[1,2-α]pyridin-7-yl]-propan-2-ol and 4-cyanobenzeneboronic acid were coupled in the same way as in Example 30 to give 2'-fluoro-5'-[8-fluoro-7-(1-hydroxy-1-methylethyl)-imidazo[1,2-α]pyridin-3-yl]biphenyl-4-carbonitrile as an off-white solid (12 mg, 10%): m/z (ES$^+$) 390 [MH$^+$].

EXAMPLE 38

2-[8-Fluoro-3-(2,2',4'-trifluorobiphenyl-5-yl)imidazo[1,2-α]pyridin-7-yl]-propan-2-ol 2-[3-(3-Chloro-4-fluorophenyl)-8-fluoroimidazo[1,2-α]pyridin-7-yl]-propan-2-ol and 2,4-difluorobenzeneboronic acid were coupled in the same way as in Example 30 to give 2-[8-fluoro-3-(2,2',4'-trifluorobiphenyl-5-yl)-imidazo[1,2-α]pyridin-7-yl]propan-2-ol as an off-white solid (3 mg, 2%):

δ$_H$ (400 MHz, d$_6$-DMSO) 1.56 (6H, s), 7.18-7.23 (2H, m), 7.34 (1H, t, J 8), 7.51 (1H, t, J 9), 7.61-7.69 (2H, m), 7.73-7.77 (2H, m), 8.36 (1H, dd, J 7 and 3); m/z (ES$^+$) 401 [MH$^+$].

EXAMPLE 39

2-[8-Fluoro-3-(2-fluoro-3'-trifluoromethylbiphenyl-5-yl) imidazo[1,2-α]pyridin-7-yl]propan-2-ol 2-[3-(3-Chloro-4-fluorophenyl)-8-fluoroimidazo [1,2-α] pyridin-7-yl]-propan-2-ol and 3-trifluoromethoxybenzeneboronic acid were coupled in the same way as in Example 30 to give 2-[8-fluoro-3-(2-fluoro-3'-trifluoromethoxybiphenyl-5-yl)imidazo[1,2-α]pyridin-7-yl]propan-2-ol as an off-white solid (4 mg, 3%): m/z (ES$^+$) 449 [MH$^+$].

EXAMPLE 40

2-[8-Fluoro-3-(2-fluoro-2'-trifluoromethylbiphenyl-5-yl) imidazo[1,2-α]pyridin-7-yl]propan-2-ol 2-[3-(3-Chloro-4-fluorophenyl)-8-fluoroimidazo[1,2-α] pyridin-7-yl]-propan-2-ol and 2-trifluoromethylbenzeneboronic acid were coupled in the same way as in Example 30 to give 2-[8-fluoro-3-(2-fluoro-2'-trifluoromethylbiphenyl-5-yl)imidazo[1,2-α]pyridin-7-yl]propan-2-ol as an off-white solid (4 mg, 3%): m/z (ES$^+$) 433 [MH$^+$].

EXAMPLE 41

2-[8-Fluoro-3-(2-fluoro-4'-vinylbiphenyl-5-yl)imidazo[1,2-α]pyridin-7-yl]-propan-2-ol 2-[3-(3-Chloro-4-fluorophenyl)-8-fluoroimidazo[1,2-α] pyridin-7-yl]-propan-2-ol and 4-vinylbenzeneboronic acid were coupled in the same way as in Example 30 to give 2-[8-fluoro-3-(2-fluoro-4'-vinylbiphenyl-5-yl)-imidazo[1,2-α]pyridin-7-yl]propan-2-ol as an off-white solid (3 mg, 3%): m/z (ES$^+$) 391 [MH$^+$].

EXAMPLE 42

2-[3-(2'-Ethoxy-2-fluorobiphenyl-5-yl)-8-fluoroimidazo[1,2-α]pyridin-7-yl]-propan-2-ol 2-[3-(3-Chloro-4-fluorophenyl)-8-fluoroimidazo[1,2-α] pyridin-7-yl]-propan-2-ol and 2-ethoxybenzeneboronic acid were coupled in the same way as in Example 30 to give 2-[3-(2'-ethoxy-2-fluorobiphenyl-5-yl)-8-fluoroimidazo[1, 2-α]pyridin-7-yl]propan-2-ol as an off-white solid (6 mg, 5%): m/z (ES$^+$) 409 [MH$^+$].

EXAMPLE 43

2-[8-Fluoro-3-(2-fluoro-2'-trifluoromethoxybiphenyl-5-yl) imidazo[1,2-α]pyridin-7-yl]propan-2-ol 2-[3-(3-Chloro-4-fluorophenyl)-8-fluoroimidazo[1,2-α] pyridin-7-yl]-propan-2-ol and 2-trifluoromethoxybenzeneboronic acid were coupled in the same way as in Example 30 to give 2-[8-fluoro-3-(2-fluoro-2'-trifluoromethoxybiphenyl-5-yl)imidazo[1,2-α]pyridin-7-yl]propan-2-ol as an off-white solid (8 mg, 6%): m/z (ES$^+$) 449 [MH$^+$].

EXAMPLE 44

2-[3-(2,4'-Difluoro-2'-methoxybiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 4-fluoro-2-methoxybenzeneboronic acid were coupled in the same way as in Example 30 to give 2-[3-(2,4'-difluoro-2'-methoxy-biphenyl-5-yl)-8-fluoroimidazo[1,2-α]pyridin-7-yl]propan-2-ol as an off-white solid (5 mg, 4%): m/z (ES$^+$) 413 [MH$^+$].

EXAMPLE 45

2,2'-Difluoro-5'-[8-fluoro-7-(1-hydroxy-1-methylethyl)imidazo[1,2-α]-pyridin-3-yl]biphenyl-4-carbonitrile 2-[3-(3-Chloro-4-fluorophenyl)-8-fluoroimidazo[1,2-α] pyridin-7-yl]-propan-2-ol and 4-(5,5-dimethyl-[1,3,2]dioxaborinan-2-yl)-3-fluorobenzonitrile were coupled in the same way as in Example 30 to give 2,2'-difluoro-5'-[8-fluoro-7-(1-hydroxy-1-methylethyl)imidazo[1,2-α]pyridin-3-yl]biphenyl-4-carbonitrile as an off-white solid (9 mg, 9%): δ$_H$ (400 MHz, d$_6$-DMSO) 1.56 (6H, s), 7.27 (1H, t, J 7), 7.60 (1H, t, J 9), 7.81-7.92 (5H, m), 8.05 (1H, d, J 10), 8.47 (1H, d, J 7); m/z (ES$^+$) 408 [MH$^+$].

EXAMPLE 46

2-[3-(4'-Dimethylamino-2-fluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 4-(N,N-dimethylamino)benzeneboronic acid were coupled in the same way as in Example 30 to give 2-[3-(4'-dimethylamino-2-fluorobiphenyl-5-yl)-8-fluoroimidazo[1,2-α]pyridin-7-yl]propan-2-ol as an off-white solid (19 mg, 10%): m/z (ES$^+$) 408 [MH$^+$].

EXAMPLE 47

2-{8-Fluoro-3-[4-fluoro-3-(1H-indol-5-yl)phenyl]imidazo [1,2-α]pyridin-7-yl}-propan-2-ol 2-[3-(3-Chloro-4-fluorophenyl)-8-fluoroimidazo[1,2-α] pyridin-7-yl]-propan-2-ol and indole-5-boronic acid-1-carboxylic acid tert-butyl ester were coupled in the same way as in Example 30 to give 5-{2-fluoro-5-[8-fluoro-7-(1-hydroxy-1-methylethyl)imidazo[1,2-α]pyridin-3-yl]phenyl}-indole-1-carboxylic acid tert-butyl ester. The residue was dissolved in methanol, and potassium carbonate was added. The reaction was heated at 50° C. overnight. The reaction was partitioned between dichloromethane and water. The organic phase was washed with water and brine, dried over anhydrous magnesium sulphate and evaporated to dryness. The residue was dissolved in dimethylsulfoside and purified by preparative HPLC to yield 2-{8-fluoro-3-[4-fluoro-3-(1H-indol-5-yl)phenyl]imidazo[1,2-α]pyridin-7-yl}propan-2-ol as an off-white solid (9 mg, 5%): m/z (ES$^+$) 404 [MH$^+$].

EXAMPLE 48

2-[3-(2,3'-Difluoro-2'-methylbiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 3-fluoro-2-methylbenzeneboronic acid were coupled in the same way as in Example 30 to give 2-[3-(2,3'-difluoro-2'-methylbiphenyl-5-yl)-8-fluor-

EXAMPLE 49

2-[3-(3'-Chloro-2-fluoro-2'-methylbiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 3-chloro-2-methylbenzeneboronic acid were coupled in the same way as in Example 30 to give 2-[3-(3'-chloro-2-fluoro-2'-methylbiphenyl-5-yl)-8-fluoroimidazo[1,2-α]pyridin-7-yl]propan-2-ol as an off-white solid (5 mg, 4%): m/z (ES$^+$) 413 [MH$^+$].

EXAMPLE 50

2-{8-Fluoro-3-[4-fluoro-3-(2-methoxypyrimidin-5-yl)phenyl]imidazo[1,2-α]pyridin-7-yl}propan-2-ol 2-[3-(3-Chloro-4-fluorophenyl)-8-fluoroimidazo[1,2-α]pyridin-7-yl]-propan-2-ol and 2-methoxypyrimidine-5-boronic acid were coupled in the same way as in Example 30 to give 2-{8-fluoro-3-[4-fluoro-3-(2-methoxypyrimidin-5-yl)phenyl]imidazo[1,2-α]pyridin-7-yl}propan-2-ol as an off-white solid (5 mg, 4%): m/z (ES$^+$) 421 [MH$^+$].

EXAMPLE 51

2-{8-Fluoro-3-[4-fluoro-3-(pyrimidin-5-yl)phenyl]imidazo[1,2-α]pyridin-7-yl}propan-2-ol 2-[3-(3-Chloro-4-fluorophenyl)-8-fluoroimidazo[1,2-α]pyridin-7-yl]-propan-2-ol and pyrimidine-5-boronic acid were coupled in the same way as in Example 30 to give 2-{8-fluoro-3-[4-fluoro-3-(pyrimidin-5-yl)phenyl]-imidazo[1,2-α]pyridin-7-yl}propan-2-ol as an off-white solid (7 mg, 6%): m/z (ES$^+$) 367 [MH$^+$].

EXAMPLE 52

2-{8-Fluoro-3-[4-fluoro-3-(2-methylquinolin-5-yl)phenyl]imidazo[1,2-α]pyridin-7-yl}propan-2-ol 2-[3-(3-Chloro-4-fluorophenyl)-8-fluoroimidazo[1,2-α]pyridin-7-yl]-propan-2-ol and 2-methylquinoline-5-boronic acid were coupled in the same way as in Example 30 to give 2-{8-fluoro-3-[4-fluoro-3-(2-methylquinolin-5-yl)phenyl]imidazo[1,2-α]pyridin-7-yl}propan-2-ol as an off-white solid (5 mg, 4%): m/z (ES$^+$) 430 [MH$^+$].

EXAMPLE 53

2-{8-Fluoro-3-[4-fluoro-3-(2-methoxypyridin-5-yl)phenyl]imidazo[1,2-α]pyridin-7-yl}propan-2-ol 2-[3-(3-Chloro-4-fluorophenyl)-8-fluoroimidazo[1,2-α]pyridin-7-yl]-propan-2-ol and 2-methoxypyridine-5-boronic acid were coupled in the same way as in Example 30 to give 2-{8-fluoro-3-[4-fluoro-3-(2-methoxypyridin-5-yl)phenyl]imidazo[1,2-α]pyridin-7-yl}propan-2-ol as an off-white solid (8 mg, 7%): m/z (ES$^+$) 396 [MH$^+$].

EXAMPLE 54

2-[3-(3'-Chloro-2,4'-difluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 3-chloro-4-fluorobenzeneboronic acid were coupled in the same way as in Example 30 to give 2-[3-(3'-chloro-2,4'-difluorobiphenyl-5-yl)-8-fluoroimidazo[1,2-α]pyridin-7-yl]propan-2-ol as an off-white solid (8 mg, 6%): m/z (ES$^+$) 417 [MH$^+$].

EXAMPLE 55

2-[3-(3'-Chloro-2-fluorobiphenyl-5-yl)-8-fluoroimidazo[1,2-α]pyridin-7-yl]-propan-2-ol 2-[3-(3-Chloro-4-fluorophenyl)-8-fluoroimidazo[1,2-α]pyridin-7-yl]-propan-2-ol and 3-chlorobenzeneboronic acid were coupled in the same way as in Example 30 to give 2-[3-(3'-chloro-2-fluorobiphenyl-5-yl)-8-fluoroimidazo[1,2-α]pyridin-7-yl]propan-2-ol as an off-white solid (5 mg, 4%): m/z (ES$^+$) 399 [MH$^+$].

EXAMPLE 56

2-[3-(2',4'-Dichloro-2-fluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 2,4-dichlorobenzeneboronic acid were coupled in the same way as in Example 30 to give 2-[3-(2',4'-dichloro-2-fluorobiphenyl-5-yl)-8-fluoroimidazo[1,2-α]pyridin-7-yl]propan-2-ol as an off-white solid (4 mg, 3%): m/z (ES$^+$) 434 [MH$^+$].

EXAMPLE 57

2-[3-(3',5'-Dichloro-2-fluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 3,5-dichlorobenzeneboronic acid were coupled in the same way as in Example 30 to give 2-[3-(3',5'-dichloro-2-fluorobiphenyl-5-yl)-8-fluoroimidazo[1,2-α]pyridin-7-yl]propan-2-ol as an off-white solid (3 mg, 2%): m/z (ES$^+$) 434 [MH$^+$].

EXAMPLE 58

2-[3-(3',4'-Dichloro-2-fluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 3,4-dichlorobenzeneboronic acid were coupled in the same way as in Example 30 to give 2-[3-(3',4'-dichloro-2-fluorobiphenyl-5-yl)-8-fluoroimidazo[1,2-α]pyridin-7-yl]propan-2-ol as an off-white solid (4 mg, 3%): m/z (ES$^+$) 434 [MH$^+$].

EXAMPLE 59

2-[8-Fluoro-3-(2-fluoro-4'-methanesulfonylbiphenyl-5-yl)imidazo[1,2-α]pyridin-7-yl]propan-2-ol 2-[3-(3-Chloro-4-fluorophenyl)-8-fluoroimidazo[1,2-α]pyridin-7-yl]-propan-2-ol and 4-methanesulfonylbenzeneboronic acid were coupled in the same way as in Example 30 to give 2-[8-fluoro-3-(2-fluoro-4'-methanesulfonylbiphenyl-5-yl)imidazo[1,2-α]pyridin-7-yl]propan-2-ol as an off-white solid (8 mg, 6%): m/z (ES$^+$) 443 [MH$^+$].

EXAMPLE 60

2-[3-(2',3'-Dichloro-2-fluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 2,3-dichlorobenzeneboronic acid were coupled in the same way as in Example 30 to give 2-[3-(2',3'-dichloro-2-fluorobiphenyl-5-yl)-8-fluoroimidazo [1,2-α]pyridin-7-yl]propan-2-ol as an off-white solid (3 mg, 2%): m/z (ES$^+$) 434 [MH$^+$].

EXAMPLE 61

2-{3-[3-(Benzo[b]thien-7-yl)-4-fluorophenyl]-8-fluoroimidazo[1,2-α]pyridin-7-yl}propan-2-ol 2-[3-(3-Chloro-4-fluorophenyl)-8-fluoroimidazo[1,2-α] pyridin-7-yl]-propan-2-ol and benzo[b]thiophene-7-boronic acid were coupled in the same way as in Example 30 to give 2-{3-[3-(benzo[b]thien-7-yl)-4-fluorophenyl]-8-fluoroimidazo[1,2-α]pyridin-7-yl}propan-2-ol as an off-white solid (4 mg, 3%): m/z (ES$^+$) 421 [MH$^+$].

EXAMPLE 62

2-{8-Fluoro-3-[2-fluoro-2'-(pyrazol-1-yl)biphenyl-5-yl]imidazo[1,2-α]pyridin-7-yl}propan-2-ol 2-[3-(3-Chloro-4-fluorophenyl)-8-fluoroimidazo[1,2-α] pyridin-7-yl]-propan-2-ol and 2-(pyrazol-1-yl)benzeneboronic acid were coupled in the same way as in Example 30 to give 2-{8-fluoro-3-[2-fluoro-2'-(pyrazol-1-yl)biphenyl-5-yl]imidazo[1,2-α]pyridin-7-yl}propan-2-ol as an off-white solid (5 mg, 4%): m/z (ES$^+$) 431 [MH$^+$].

EXAMPLE 63

2-{8-Fluoro-3-[4-fluoro-3-(3-phenylisoxazol-5-yl)phenyl] imidazo[1,2-α]pyridin-7-yl}propan-2-ol 2-[3-(3-Chloro-4-fluorophenyl)-8-fluoroimidazo[1,2-α] pyridin-7-yl]-propan-2-ol and 3-phenylisoxazole-5-boronic acid were coupled in the same way as in Example 30 to give 2-{8-fluoro-3-[4-fluoro-3-(3-phenylisoxazol-5-yl)phenyl] imidazo[1,2-α]pyridin-7-yl}propan-2-ol as an off-white solid (6 mg, 5%): m/z (ES$^+$) 432 [MH$^+$].

EXAMPLE 64

2-{8-Fluoro-3-[4-fluoro-3-(isoquinolin-5-yl)phenyl]imidazo[1,2-α]pyridin-7-yl}propan-2-ol 2-[3-(3-Chloro-4-fluorophenyl)-8-fluoroimidazo[1,2-α] pyridin-7-yl]-propan-2-ol and isoquinoline-5-boronic acid were coupled in the same way as in Example 30 to give 2-{8-fluoro-3-[4-fluoro-3-(isoquinolin-5-yl)phenyl]imidazo [1,2-α]pyridin-7-yl}propan-2-ol as an off-white solid (7 mg, 5%): m/z (ES$^+$) 416 [MH$^+$].

EXAMPLE 65

2-[8-Fluoro-3-(2,3',5'-trifluorobiphenyl-5-yl)imidazo[1,2-α]pydridin-7-yl]propan-2-ol 2-[3-(3-Chloro-4-fluorophenyl)-8-fluoroimidazo[1,2-α] pyridin-7-yl]-propan-2-ol and 3,5-difluorobenzeneboronic acid were coupled in the same way as in Example 30 to give 2-[8-fluoro-3-(2,3',5'-trifluorobiphenyl-5-yl)imidazo[1,2-α] pyridin-7-yl]propan-2-ol as an off-white solid (5 mg, 3%): m/z (ES$^+$) 401 [MH$^+$].

EXAMPLE 66

2-[8-Fluoro-3-(2-fluoro-3'-isopropylbiphenyl-5-yl)imidazo [1,2-α]pyridin-7-yl]propan-2-ol 2-[3-(3-Chloro-4-fluorophenyl)-8-fluoroimidazo[1,2-α] pyridin-7-yl]-propan-2-ol and 3-isopropylbenzeneboronic acid were coupled in the same way as in Example 30 to give 2-[8-fluoro-3-(2-fluoro-3'-isopropylbiphenyl-5-yl)imidazo [1,2-α]pyridin-7-yl]propan-2-ol as an off-white solid (7 mg, 4%): m/z (ES$^+$) 406 [MH$^+$].

EXAMPLE 67

2-[8-Fluoro-3-(2,3',4'-trifluorobiphenyl-5-yl)imidazo[1,2-α]pyridin-7-yl]-propan-2-ol 2-[3-(3-Chloro-4-fluorophenyl)-8-fluoroimidazo[1,2-α] pyridin-7-yl]-propan-2-ol and 3,4-difluorobenzeneboronic acid were coupled in the same way as in Example 30 to give 2-[8-fluoro-3-(2,3',4'-trifluorobiphenyl-5-yl)-imidazo[1,2-α]pyridin-7-yl]propan-2-ol as an off-white solid (6 mg, 3%): m/z (ES$^+$) 401 [MH$^+$].

EXAMPLE 68

2-{8-Fluoro-3-[4-fluoro-3-(quinolin-5-yl)phenyl]imidazo [1,2-α]pyridin-7-yl}propan-2-ol 2-[3-(3-Chloro-4-fluorophenyl)-8-fluoroimidazo[1,2-α] pyridin-7-yl]-propan-2-ol and quinoline-5-boronic acid were coupled in the same way as in Example 30 to give 2-{8-fluoro-3-[4-fluoro-3-(quinolin-5-yl)phenyl]-imidazo [1,2-α]pyridin-7-yl}propan-2-ol as an off-white solid (7 mg, 5%): m/z (ES$^+$) 416 [MH$^+$].

EXAMPLE 69

2-[3-(3'-Chloro-2,2'-difluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 3-chloro-2-fluorobenzeneboronic acid were coupled in the same way as in Example 30 to give 2-[3-(3'-chloro-2,2'-difluorobiphenyl-5-yl)-8-fluoroimidazo[1,2-α]pyridin-7-yl]propan-2-ol as an off-white solid (5 mg, 3%): m/z (ES$^+$) 417 [MH$^+$].

EXAMPLE 70

2-[3-(5'-Chloro-2,2'-difluorobiphenyl-5-yl)-8-fluoroimidazo[1,2-α]pyridin-7-yl]propan-2-ol 2-[3-(3-Chloro-4-fluorophenyl)-8-fluoroimidazo[1,2-α] pyridin-7-yl]-propan-2-ol and 2-(5-chloro-2-fluorophenyl)-5,5-dimethyl-[1,3,2]dioxaborinane were coupled in the same way as in Example 30 to give 2-[3-(5'-chloro-2,2'-difluorobiphenyl-5-yl)-8-fluoroimidazo[1,2-α]pyridin-7-yl] propan-2-ol as an off-white solid (6 mg, 3%): m/z (ES$^+$) 417 [MH$^+$].

EXAMPLE 71

4,2'-Difluoro-5'-[8-fluoro-7-(1-hydroxy-1-methylethyl)imidazo[1,2-α]pyridin-3-yl]biphenyl-3-carbonitrile 2-[3-(3-Chloro-4-fluorophenyl)-8-fluoroimidazo[1,2-α] pyridin-7-yl]-propan-2-ol and 5-(5,5-dimethyl-[1,3,2]dioxaborinan-2-yl)-2-fluorobenzonitrile were coupled in the same way as in Example 30 to give 4,2'-difluoro-5'-[8- fluoro-7-(1-hydroxy-1-methylethyl)imidazo[1,2-α]pyridin-3-yl]biphenyl-3-carbonitrile as an off-white solid (9 mg, 5%): m/z (ES$^+$) 408 [MH$^+$].

EXAMPLE 72

2-{8-Fluoro-3-[4-fluoro-3-(fur-2-yl)phenyl]imidazo[1,2-α]pyridin-7-yl}-propan-2-ol 2-[3-(3-Chloro-4-fluorophenyl)-8-fluoroimidazo[1,2-α]pyridin-7-yl]-propan-2-ol and furan-2-boronic acid were coupled in the same way as in Example 30 to give 2-{8-fluoro-3-[4-fluoro-3-(fur-2-yl)phenyl]imidazo[1,2-α]pyridin-7-yl}propan-2-ol as an off-white solid (6 mg, 4%): m/z (ES$^+$) 355 [MH$^+$].

EXAMPLE 73

2-{3-[3-(Benzo[1,3]dioxol-5-yl)-4-fluorophenyl]-8-fluoroimidazo[1,2-α]pyridin-7-yl}propan-2-ol 2-[3-(3-Chloro-4-fluorophenyl)-8-fluoroimidazo[1,2-α]pyridin-7-yl]-propan-2-ol and benzo[1,3]dioxole-5-boronic acid were coupled in the same way as in Example 30 to give 2-{3-[3-(benzo[1,3]dioxol-5-yl)-4-fluorophenyl]-8-fluoroimidazo[1,2-α]pyridin-7-yl}propan-2-ol as an off-white solid (8 mg, 4%): m/z (ES$^+$) 409 [MH$^+$].

EXAMPLE 74

2-[8-Fluoro-3-(2-fluoro-3'-trifluoromethylbiphenyl-5-yl)imidazo[1,2-α]pyridin-7-yl]propan-2-ol 2-[3-(3-Chloro-4-fluorophenyl)-8-fluoroimidazo[1,2-α]pyridin-7-yl]-propan-2-ol and 3-trifluoromethylbenzeneboronic acid were coupled in the same way as in Example 30 to give 2-[8-fluoro-3-(2-fluoro-3'-trifluoromethylbiphenyl-5-yl)imidazo[1,2-α]pyridin-7-yl]propan-2-ol as an off-white solid (7 mg, 4%): m/z (ES$^+$) 433 [MH$^+$].

EXAMPLE 75

2-{8-Fluoro-3-[4-fluoro-3-(1H-pyrrol-2-yl)phenyl]imidazo[1,2-α]pyridin-7-yl}propan-2-ol 2-[3-(3-Chloro-4-fluorophenyl)-8-fluoroimidazo[1,2-α]pyridin-7-yl]-propan-2-ol and pyrrole-2-boronic acid-1-dicarboxylic acid 1-tert-butyl ester were coupled in the same way as in Example 30 to give 2-{8-fluoro-3-[4-fluoro-3-(1H-pyrrol-2-yl)phenyl]imidazo[1,2-α]pyridin-7-yl}propan-2-ol as an off-white solid (9 mg, 5%): m/z (ES$^+$) 354 [MH$^+$].

EXAMPLE 76

2-{3-[3-(Benzofur-2-yl)-4-fluorophenyl]-8-fluoroimidazo[1,2-α]pyridin-7-yl}propan-2-ol 2-[3-(3-Chloro-4-fluorophenyl)-8-fluoroimidazo[1,2-α]pyridin-7-yl]-propan-2-ol and benzofuran-2-boronic acid were coupled in the same way as in Example 30 to give 2-{3-[3-(benzofuran-2-yl)-4-fluorophenyl]-8-fluoroimidazo[1,2-α]pyridin-7-yl}propan-2-ol as an off-white solid (6 mg, 3%): m/z (ES$^+$) 405 [MH$^+$].

EXAMPLE 77

2-[3-(2,2'-Difluoro-4'-methoxybiphenyl-5-yl)-8-fluoroimidazo[1,2-α]pyridin-7-yl]propan-2-ol 2-[3-(3-Chloro-4-fluorophenyl)-8-fluoroimidazo[1,2-α]pyridin-7-yl]-propan-2-ol and 2-(2-fluoro-4-methoxyphenyl)-4,4,5,5-tetramethyl-[1,3,2]dioxaborolane were coupled in the same way as in Example 30 to give 2-[3-(2,2'-difluoro-4'-methoxybiphenyl-5-yl)-8-fluoroimidazo[1,2-α]pyridin-7-yl]propan-2-ol as an off-white solid (5 mg, 3%): m/z (ES$^+$) 413 [MH$^+$].

EXAMPLE 78

2-[8-Fluoro-3-(2-fluoro-2'-methoxybiphenyl-5-yl)imidazo[1,2-α]pyridin-7-yl]propan-2-ol 2-[3-(3-Chloro-4-fluorophenyl)-8-fluoroimidazo[1,2-α]pyridin-7-yl]-propan-2-ol and 2-methoxybenzeneboronic acid were coupled in the same way as in Example 30 to give 2-[8-fluoro-3-(2-fluoro-2'-methoxybiphenyl-5-yl)imidazo[1,2-α]pyridin-7-yl]propan-2-ol as an off-white solid (8 mg; 7%): m/z (ES$^+$) 395 [MH$^+$].

EXAMPLE 79

4,2'-Difluoro-5'-(8-fluoro-7-trifluoromethylimidazo[1,2-α]pyridin-3-yl)-biphenyl-2-carbonitrile A mixture of 2-chloro-3-fluoro-4-trifluoromethylpyridine (3.50 g, 17.5 mmol), benzophenone imine (3.50 g, 19.3 mmol), palladium(II) acetate (0.158 g, 0.70 mmol), caesium carbonate (8.00 g, 24.6 mmol) and BINAP (0.66 g, 1.05 mmol) was suspended in toluene (35 ml) and degassed with nitrogen for 1 h. The mixture was then heated at 115° C. for 18 h. The mixture was allowed to cool to ambient temperature, diluted with toluene (100 ml) and the organic phase was washed with water (100 ml) and brine (100 ml), dried over anhydrous sodium sulphate, filtered and evaporated to give an orange oil. The oil was dissolved in propan-2-ol (60 ml), 5N hydrochloric acid (10 ml) added and the mixture heated at 50° C. for 30 min. The mixture was cooled to ambient temperature and solid sodium hydrogencarbonate (7.14 g, 85 mmol) added portionwise over 10 min, followed by addition of chloroacetaldehyde (2.75 g, 35.08 mmol). On complete addition the mixture was heated at 95° C. for 24 h. The mixture was allowed to cool to ambient temperature, filtered through a glass microfibre filter paper, the solid washed with ethanol (30 ml) and the filtrate evaporated. The residue was diluted with ethyl acetate (200 ml) and extracted with 5N hydrochloric acid (2×75 ml). The organics were filtered and then washed with ethyl acetate (2×100 ml). The aqueous phase was then made basic by the addition of solid sodium hydrogen-carbonate and extracted with ethyl acetate (2×150 ml). The organics were washed with brine (100 ml), dried over anhydrous sodium sulphate, filtered and evaporated to give a brown oil. The oil was purified by flash column chromatography on silica eluting with dichloromethane on a gradient of methanol (0-2%). Collecting appropriate fractions gave 8-fluoro-7-trifluoromethylimidazo[1,2-α]pyridine (1.5 g, 42%) as a pale yellow solid: $\delta_H$ (360 MHz, CDCl$_3$) 6.92 (1H, dd, J 7 and 7), 7.75 (1H, d, J 3), 7.80 (1H, d, J 3), 8.04 (1H, d, J 7).

8-Fluoro-7-trifluoromethylimidazo[1,2-α]pyridine (102 mg, 0.5 mmol) and 5'-bromo-4,2'-difluorobiphenyl-2-carbonitrile (221 mg, 0.75 mmol) were coupled following the procedure given in Example 6 to afford 4,2'-difluoro-5'-(8- fluoro-7-trifluoromethylimidazo[1,2-α]pyridin-3-yl)-biphenyl-2-carbonitrile (93 mg, 45%) as an off-white solid: $\delta_H$ (360 MHz, CDCl$_3$) 7.00 (1H, dd, J 7 and 6), 7.40-7.47 (2H, m), 7.55 (1H, dd, J 8 and 3), 7.57-7.65 (3H, m), 7.86 (1H, s), 8.34 (1H, d, J 7); m/z (ES$^+$) 418 (100%, [MH]$^+$).

EXAMPLE 80

6,2'-Difluoro-5'-(8-fluoro-7-trifluoromethylimidazo[1,2-α]pyridin-3-yl)-biphenyl-2-carbonitrile 8-Fluoro-7-trifluoromethylimidazo[1,2-α]pyridine (102 mg, 0.5 mmol) and 5'-bromo-6,2'-difluorobiphenyl-2-carbonitrile (221 mg, 0.75 mmol) were coupled following the procedure given in Example 6 to afford 6,2'-difluoro-5'-(8-fluoro-7-trifluoromethylimidazo[1,2-α]pyridin-3-yl)-biphenyl-2-carbonitrile (65 mg, 31%) as a white solid: $\delta_H$ (360 MHz, CDCl$_3$) 6.99 (1H, dd, J 7 and 6), 7.41-7.51 (2H, m), 7.54-7.60 (1H, m), 7.62-7.69 (3H, m), 7.87 (1H, s), 8.33 (1H, d, J 7); m/z (ES$^+$) 418 (100%, [MH]$^+$).

EXAMPLE 81

3-[3-(3,5-Difluoropyridin-2-yl)-4-fluorophenyl]-8-fluoro-7-trifluoromethylimidazo[1,2-α]pyridine 8-Fluoro-7-trifluoromethylimidazo[1,2-α]pyridine (102 mg, 0.5 mmol) and 2-(5-bromo-2-fluorophenyl)-3,5-difluoropyridine (216 mg, 0.75 mmol) were coupled following the procedure given in Example 6 to afford 3-[3-(3,5-difluoropyridin-2-yl)-4-fluorophenyl]-8-fluoro-7-trifluoromethylimidazo[1,2-α]pyridine (65 mg, 32%) as an off-white solid: $\delta_H$ (360 MHz, CDCl$_3$) 6.97 (1H, dd, J 7 and 6), 7.35-7.42 (2H, m), 7.61-7.65 (1H, m), 7.78 (1H, dd, J 7 and 2), 7.87 (1H, s), 8.16 (1H, d, J 7), 8.49 (1H, d, J 2); m/z (ES$^+$) 412 (100%, [MH]$^+$).

EXAMPLE 82

2-[2-Fluoro-5-(8-fluoro-7-trifluoromethylimidazo[1,2-α]pyridin-3-yl)-phenyl]nicotinonitrile 8-Fluoro-7-trifluoromethylimidazo[1,2-α]pyridine (102 mg, 0.5 mmol) and 2-(5-bromo-2-fluorophenyl)nicotinonitrile (208 mg, 0.75 mmol) were coupled following the procedure given in Example 6 to afford 2-[2-fluoro-5-(8-fluoro-7-trifluoromethylimidazo[1,2-α]pyridin-3-yl)phenyl]-nicotinonitrile (91 mg, 45%) as a white solid: $\delta_H$ (360 MHz, CDCl$_3$) 6.98 (1H, dd, J 7 and 6), 7.44-7.54 (2H, m), 7.67-7.72 (1H, m), 7.79 (1H, dd, J 7 and 2), 7.88 (1H, s), 8.15 (1H, dd, J 7 and 2), 8.24 (1H, d, J 7), 8.95 (1H, d, J 2); m/z (ES$^+$) 401 (100%, [MH]$^+$).

EXAMPLE 83

1-[2-Fluoro-5-(8-fluoro-7-trifluoromethylimidazo[1,2-α]pyridin-3-yl)-phenyl]pyrrolidin-2-one 8-Fluoro-7-trifluoromethylimidazo[1,2-α]pyridine was coupled to 1-(5-bromo-2-fluorophenyl)pyrrolidin-2-one as described in Example 6 to give 1-[2-fluoro-5-(8-fluoro-7-trifluoromethylimidazo[1,2-α]pyridin-3-yl)-phenyl]pyrrolidin-2-one as a white solid (90 mg, 24%): m/z (ES$^+$) 382 [MH$^+$].

EXAMPLE 84

3-(2,4'-Difluoro-2'-methanesulfonylbiphenyl-5-yl)-8-fluoro-7-trifluoromethylimidazo[1,2-α]pyridine 5'-Bromo-4,2'-difluoro-2-methanesulfonylbiphenyl was converted to 2-(2,4'-difluoro-2'-methanesulfonylbiphenyl-5-yl)-4,4,5,5-tetramethyl-[1,3,2]dioxaborolane following the procedure in Example 2: $\delta_H$ (400 MHz, CDCl$_3$) 1.33 (12H, s), 2.87 (3H, s), 7.14 (1H, dd, J 8 and 2), 7.37 (2H, dd, J 7 and 2), 7.76 (1H, dd, J 8 and 2), 7.86-7.93 (2H, m).

8-Fluoro-7-trifluoromethylimidazo[1,2-α]pyridine was brominated in the same way as in Example 1 to give 3-bromo-8-fluoro-7-trifluoromethylimidazo[1,2-α]pyridine as an off-white solid (2.2 g, 66%): $\delta_H$ (400 MHz, CDCl$_3$) 7.09 (1H, dd, J 7 and 6), 7.79 (1H, s), 8.04 (1H, d, J 7); m/z (ES$^+$) 283 [MH$^+$].

3-Bromo-8-fluoro-7-trifluoromethylimidazo[1,2-α]pyridine was coupled to 2-(2,4'-difluoro-2'-methanesulfonylbiphenyl-5-yl)-4,4,5,5-tetramethyl-[1,3,2]dioxaborolane as described in Example 1 to give 3-(2,4'-difluoro-2'-methanesulfonylbiphenyl-5-yl)-8-fluoro-7-trifluoromethylimidazo[1,2-α]pyridine as a white solid (147 mg, 42%): $\delta_H$ (400 MHz, CDCl$_3$) 2.91 (3H, s), 6.99 (1H, dd, J 7 and 6), 7.35-7.47 (3H, m), 7.61-7.65 (2H, m), 7.85 (1H, s), 7.98-8.01 (1H, m), 8.48 (11H, d, J 7); m/z (ES$^+$) 471 [MH$^+$].

EXAMPLE 85

2-{8-Fluoro-3-[4-fluoro-3-(2-methyl-2H-[1,2,4]triazol-3-ylmethoxy)phenyl]-imidazo[1,2-α]pyridin-7-yl}propan-2-ol 3-(5-Bromo-2-fluorophenoxymethyl)-2-methyl-2H-[1,2,4]triazole was prepared as described in Example 28: $\delta_H$ (360 MHz, CDCl$_3$) 4.01 (3H, s), 5.29 (2H, s), 6.96-6.99 (1H, m), 7.09-7.13 (1H, m), 7.29 (1H, dd, J 5 and 2), 7.88 (1H, s); m/z (ES$^+$) 288 [MH$^+$].

2-(8-Fluoroimidazo[1,2-α]pyridin-7-yl)propan-2-ol was coupled to 3-(5-bromo-2-fluorophenoxymethyl)-2-methyl-2H-[1,2,4]triazole as described in Example 6 to give 2-{8-fluoro-3-[4-fluoro-3-(2-methyl-2H-[1,2,4]triazol-3-ylmethoxy)phenyl]imidazo[1,2-α]pyridin-7-yl}propan-2-ol as an off-white solid (169 mg, 43%): $\delta_H$ (400 MHz, d$_6$-DMSO) 1.58 (6H, d, J 1), 3.94 (3H, s), 5.53 (2H, s), 5.55 (1H, s), 7.21-7.29 (2H, m), 7.44 (1H, dd, J 11 and 9), 7.68 (1H, dd, J 8 and 2), 7.76 (1H, s), 7.98 (1H, s), 8.42 (1H, d, J 7); m/z (ES$^+$) 400 [MH$^+$].

EXAMPLE 86

8-Fluoro-3-[4-fluoro-3-(1-methyl-1H-[1,2,3]triazol-4-ylmethoxy)phenyl]-7-trifluoromethylimidazo[1,2-α]pyridine 8-Fluoro-7-trifluoromethylimidazo[1,2-α]pyridine was coupled to 4-(5-bromo-2-fluorophenoxymethyl)-1-methyl-1H-[1,2,3]triazole as described in Example 6 to give 8-fluoro-3-[4-fluoro-3-(1-methyl-1H-[1,2,3]triazol-4-ylmethoxy)phenyl]-7-trifluoromethylimidazo[1,2-α]pyridine as an off-white solid: $\delta_H$ (400 MHz, d$_6$-DMSO) 4.07 (3H, s), 5.53 (2H, s), 7.14 (1H, dd, J 7 and 7), 7.29-7.31 (1H, m), 7.44 (1H, dd, J 11 and 8), 7.73 (1H, dd, J 8 and 2), 8.06 (1H, s), 8.23 (1H, s), 8.62 (1H, d, J 7); m/z (ES$^+$) 410 [MH$^+$].

The invention claimed is:

1. A compound of the formula I, or a pharmaceutically acceptable salt thereof:

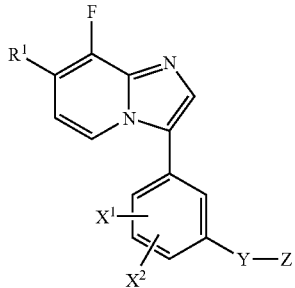

(I)

wherein:
X¹ represents hydrogen, halogen, $C_{1-6}$ alkyl, trifluoromethyl or $C_{1-6}$ alkoxy;
X² represents hydrogen or halogen;
Y represents a chemical bond, an oxygen atom, or a —NH— or —OCH₂— linkage;
Z represents an optionally substituted aryl or heteroaryl group, or a pyrrolidinonyl group;
R¹ represents hydrogen, hydrocarbon, a heterocyclic group, halogen, cyano, trifluoromethyl, nitro, —OR$^a$, —SR$^a$, —SOR$^a$, —SO₂R$^a$, —SO₂NR$^a$R$^b$, —NR$^a$COR$^b$, —NR$^a$CO₂R$^b$, —COR$^a$, —CO₂R$^a$, —CONR$^a$R$^b$ or —CR$^a$=NOR$^b$; and
R$^a$ and R$^b$ independently represent hydrogen, hydrocarbon or a heterocyclic group.

2. The compound of claim 1 of the formula IIA, or a pharmaceutically acceptable salt thereof:

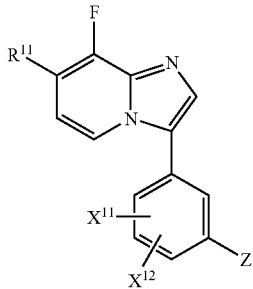

(IIA)

wherein:
X¹¹ represents hydrogen, fluoro, chloro, methyl, trifluoromethyl or methoxy;
X¹² represents hydrogen or fluoro;
R¹¹ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$) alkyl, $C_{1-6}$ alkoxy($C_{1-6}$)alkyl, di($C_{1-6}$)alkoxy($C_{1-6}$) alkyl, cyano($C_{1-6}$)alkyl, $C_{2-6}$ alkoxycarbonyl($C_{1-6}$) alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —CR⁴=NOR⁵;
R⁴ represents hydrogen or $C_{1-6}$ alkyl; and
R⁵ represents hydrogen, $C_{1-6}$ alkyl, hydroxy($C_{1-6}$)alkyl or di($C_{1-6}$)alkylamino($C_{1-6}$)alkyl.

3. The compound of claim 2 of the formula IIB, or a pharmaceutically acceptable salt thereof:

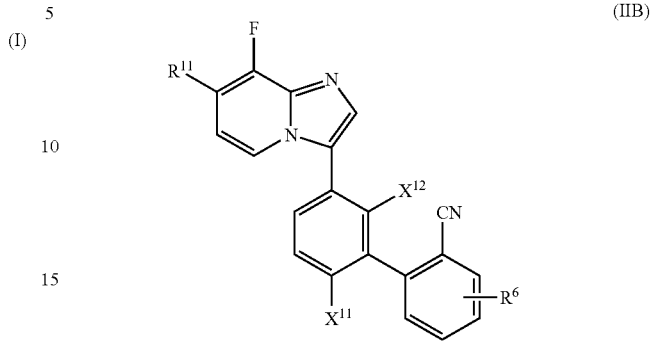

(IIB)

wherein R⁶ represents hydrogen or fluoro.

4. The compound of claim 2 of the formula IIC, or a pharmaceutically acceptable salt thereof:

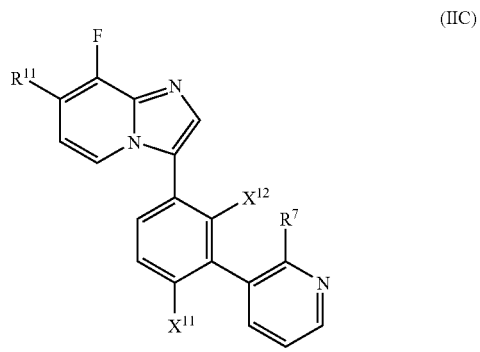

(IIC)

wherein R⁷ represents hydrogen, fluoro, cyano or methyl.

5. The compound of claim 2 of the formula IID, or a pharmaceutically acceptable salt thereof:

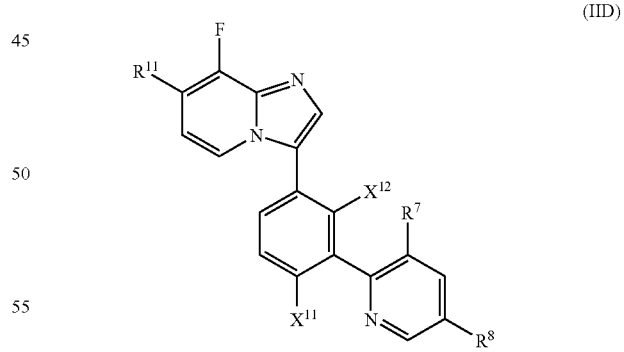

(IID)

wherein:
R⁷ represents hydrogen, fluoro, cyano or methyl; and
R⁸ represents hydrogen or fluoro.

6. A compound which is selected from:
8-fluoro-3-[3-(pyridin-3-yl)phenyl]imidazo[1,2-α]pyridine;
2-[8-fluoro-3-[4-fluoro-3-(pyridin-3-yl)phenyl]imidazo[1,2-α]pyridin-7-yl]propan-2-ol;
2'-fluoro-5'-[8-fluoro-7-(2-hydroxyprop-2-yl)imidazo[1,2-α]pyridin-3-yl]biphenyl-2-carbonitrile;

7-chloro-8-fluoro-3-[4-fluoro-3-(pyridin-3-yl)phenyl]imidazo[1,2-α]pyridine;
5'-[7-chloro-8-fluoroimidazo[1,2-α]pyridin-3-yl]-2'-fluorobiphenyl-2-carbonitrile;
4,2'-difluoro-5'-[8-fluoro-7-(1-hydroxy-1-methylethyl)imidazo[1,2-α]pyridin-3-yl]biphenyl-2-carbonitrile;
2-{3-[3-(3,5-difluoropyridin-2-yl)-4-fluorophenyl]-8-fluoroimidazo[1,2-α]pyridin-7-yl}propan-2-ol;
6,2'-difluoro-5'-[8-fluoro-7-(1-hydroxy-1-methylethyl)imidazo[1,2-α]pyridin-3-yl]biphenyl-2-carbonitrile;
2-{2-fluoro-5-[8-fluoro-7-(1-hydroxy-1-methylethyl)imidazo[1,2-α]pyridin-3-yl]phenyl}nicotinonitrile;
or a pharmaceutically acceptable salt thereof.

7. A compound which is selected from:
3,2'-difluoro-5'-[8-fluoro-7-(1-hydroxy-1-methylethyl)imidazo[1,2-α]pyridin-3-yl]biphenyl-2-carbonitrile;
4-fluoro-3'-[8-fluoro-7-(1-hydroxy-1-methylethyl)imidazo[1,2-α]pyridin-3-yl]biphenyl-2-carbonitrile;
4,2'-difluoro-5'-(8-fluoroimidazo[1,2-α]pyridin-3-yl)biphenyl-2-carbonitrile;
5'-(7-chloro-8-fluoroimidazo[1,2-α]pyridin-3-yl)-4,2'-difluorobiphenyl-2-carbonitrile;
3-(2'-cyano-2,4'-difluorobiphenyl-5-yl)-8-fluoroimidazo[1,2-α]pyridine-7-carboxylic acid methyl ester;
4,2'-difluoro-5'-[8-fluoro-7-(1-fluoro-1-methylethyl)imidazo[1,2-α]pyridin-3-yl]biphenyl-2-carbonitrile;
4'-fluoro-3'-[8-fluoro-7-(1-hydroxy-1-methylethyl)imidazo[1,2-α]pyridin-3-yl]biphenyl-2-carbonitrile;
3'-fluoro-5'-[8-fluoro-7-(1-hydroxy-1-methylethyl)imidazo[1,2-α]pyridin-3-yl]biphenyl-2-carbonitrile;
2-{3-[3-(3,5-difluoropyridin-4-yl)-4-fluorophenyl]-8-fluoroimidazo[1,2-α]pyridin-7-yl}propan-2-ol;
5,2'-difluoro-5'-[8-fluoro-7-(1-hydroxy-1-methylethyl)imidazo[1,2-α]pyridin-3-yl]biphenyl-2-carbonitrile;
2-fluoro-3'-[8-fluoro-7-(1-hydroxy-1-methylethyl)imidazo[1,2-α]pyridin-3-yl]biphenyl-2-carbonitrile;
3'-[8-fluoro-7-(1-hydroxy-1-methylethyl)imidazo[1,2-α]pyridin-3-yl]-6,2',6'-trifluorobiphenyl-2-carbonitrile;
4,4'-difluoro-3'-[8-fluoro-7-(1-hydroxy-1-methylethyl)imidazo[1,2-α]pyridin-3-yl]biphenyl-2-carbonitrile;
3-chloro-2'-fluoro-5'-[8-fluoro-7-(1-hydroxy-1-methylethyl)imidazo[1,2-α]pyridin-3-yl]biphenyl-4-carbonitrile;
1-{2-fluoro-5-[8-fluoro-7-(1-hydroxy-1-methylethyl)imidazo[1,2-a]pyridin-3-yl]phenyl}pyrrolidin-2-one;
2-{8-fluoro-3-[4-fluoro-3-(imidazol-1-yl)phenyl]imidazo[1,2-a]pyridin-7-yl}-propan-2-ol;
4,3'-difluoro-5'-[8-fluoro-7-(1-hydroxy-1-methylethyl)imidazo[1,2-α]pyridin-3-yl]biphenyl-2-carbonitrile;
3'-[8-fluoro-7-(1-hydroxy-1-methylethyl)imidazo[1,2-α]pyridin-3-yl]-4,2',6'-trifluorobiphenyl-2-carbonitrile;
2-{8-fluoro-3-[4-fluoro-3-(1-methyl-1H-[1,2,3]triazol-4-ylmethoxy)phenyl]-imidazo[1,2-α]pyridin-7-yl}propan-2-ol;
3-(2,4'-difluoro-2'-methanesulfonylbiphenyl-5-yl)-8-fluoro-7-(1-hydroxy-1-methylethyl)imidazo[1,2-α]pyridine;
1-{2'-fluoro-5'-[8-fluoro-7-(1-hydroxy-1-methylethyl)imidazo[1,2-α]pyridin-3-yl]biphenyl-4-yl}ethanone;
2-[3-(2,4'-difluoro-2'-methylbiphenyl-5-yl)-8-fluoroimidazo[1,2-α]pyridin-7-yl]propan-2-ol;
2'-fluoro-5'-[8-fluoro-7-(1-hydroxy-1-methylethyl)imidazo[1,2-']pyridin-3-yl]biphenyl-3-carbonitrile;
1-{2'-fluoro-5'-[8-fluoro-7-(1-hydroxy-1-methylethyl)imidazo[1,2-α]pyridin-3-yl]biphenyl-3-yl}ethanone;
2-[8-fluoro-3-(2-fluoro-5'-isopropyl-2'-methoxybiphenyl-5-yl)imidazo[1,2-α]pyridin-7-yl]propan-2-ol;
2'-fluoro-5'-[8-fluoro-7-(1-hydroxy-1-methylethyl)imidazo[1,2-α]pyridin-3-yl]biphenyl-4-carbaldehyde;
2-[8-fluoro-3-(2-fluoro-4'-trifluoromethylbiphenyl-5-yl)imidazo[1,2-α]pyridin-7-yl]propan-2-ol;
2'-fluoro-5'-[8-fluoro-7-(1-hydroxy-1-methylethyl)imidazo[1,2-α]pyridin-3-yl]biphenyl-4-carbonitrile;
2-[8-fluoro-3-(2,2',4'-trifluorobiphenyl-5-yl)imidazo[1,2-α]pyridin-7-yl]-propan-2-ol;
2-[8-fluoro-3-(2-fluoro-3'-trifluoromethoxybiphenyl-5-yl)imidazo[1,2-α]pyridin-7-yl]propan-2-ol;
2-[8-fluoro-3-(2-fluoro-2'-trifluoromethylbiphenyl-5-yl)imidazo[1,2-α]pyridin-7-yl]propan-2-ol;
2-[8-fluoro-3-(2-fluoro-4'-vinylbiphenyl-5-yl)imidazo[1,2-α]pyridin-7-yl]-propan-2-ol;
2-[3-(2'-ethoxy-2-fluorobiphenyl-5-yl)-8-fluoroimidazo[1,2-α]pyridin-7-yl]-propan-2-ol;
2-[8-fluoro-3-(2-fluoro-2'-trifluoromethoxybiphenyl-5-yl)imidazo[1,2-α]pyridin-7-yl]propan-2-ol;
2-[3-(2,4'-difluoro-2'-methoxybiphenyl-5-yl)-8-fluoroimidazo[1,2-α]pyridin-7-yl]propan-2-ol;
2,2'-difluoro-5'-[8-fluoro-7-(1-hydroxy-1-methylethyl)imidazo[1,2-α]pyridin-3-yl]biphenyl-4-carbonitrile;
2-[3-(4'-dimethylamino-2-fluorobiphenyl-5-yl)-8-fluoroimidazo[1,2-α]pyridin-7-yl]propan-2-ol;
2-{8-fluoro-3-[4-fluoro-3-(1H-indol-5-yl)phenyl]imidazo[1,2-α]pyridin-7-yl}-propan-2-ol;
2-[3-(2,3'-difluoro-2'-methylbiphenyl-5-yl)-8-fluoroimidazo[1,2-α]pyridin-7-yl]propan-2-ol;
2-[3-(3'-chloro-2-fluoro-2'-methylbiphenyl-5-yl)-8-fluoroimidazo[1,2-α]pyridin-7-yl]propan-2-ol;
2-{8-fluoro-3-[4-fluoro-3-(2-methoxypyrimidin-5-yl)phenyl]imidazo[1,2-α]pyridin-7-yl}propan-2-ol;
2-{8-fluoro-3-[4-fluoro-3-(pyrimidin-5-yl)phenyl]imidazo[1,2-α]pyridin-7-yl}-propan-2-ol;
2-{8-fluoro-3-[4-fluoro-3-(2-methylquinolin-5-yl)phenyl]imidazo[1,2-α]pyridin-7-yl}propan-2-ol;
2-{8-fluoro-3-[4-fluoro-3-(2-methoxypyridin-5-yl)phenyl]imidazo[1,2-α]pyridin-7-yl}propan-2-ol;
2-[3-(3'-chloro-2,4'-difluorobiphenyl-5-yl)-8-fluoroimidazo[1,2-α]pyridin-7-yl]propan-2-ol;
2-[3-(3'-chloro-2-fluorobiphenyl-5-yl)-8-fluoroimidazo[1,2-α]pyridin-7-yl]-propan-2-ol;
2-[3-(2',4'-dichloro-2-fluorobiphenyl-5-yl)-8-fluoroimidazo[1,2-α]pyridin-7-yl]propan-2-ol;
2-[3-(3',5'-dichloro-2-fluorobiphenyl-5-yl)-8-fluoroimidazo[1,2-α]pyridin-7-yl]propan-2-ol;
2-[3-(3',4'-dichloro-2-fluorobiphenyl-5-yl)-8-fluoroimidazo[1,2-α]pyridin-7-yl]propan-2-ol;
2-[8-fluoro-3-(2-fluoro-4'-methanesulfonylbiphenyl-5-yl)imidazo[1,2-α]pyridin-7-yl]propan-2-ol;
2-[3-(2',3'-dichloro-2-fluorobiphenyl-5-yl)-8-fluoroimidazo[1,2-α]pyridin-7-yl]propan-2-ol;
2-{3-[3-(benzo[b]thien-7-yl)-4-fluorophenyl]-8-fluoroimidazo[1,2-α]pyridin-7-yl}propan-2-ol;
2-{8-fluoro-3-[2-fluoro-2'-(pyrazol-1-yl)biphenyl-5-yl)imidazo[1,2-α]pyridin-7-yl}propan-2-ol;
2-{8-fluoro-3-[4-fluoro-3-(3-phenylisoxazol-5-yl)phenyl]imidazo[1,2-α]pyridin-7-yl}propan-2-ol;
2-{8-fluoro-3-[4-fluoro-3-(isoquinolin-5-yl)phenyl]imidazo[1,2-α]pyridin-7-yl}propan-2-ol;
2-[8-fluoro-3-(2,3',5'-trifluorobiphenyl-5-yl)imidazo[1,2-α]pyridin-7-yl]propan-2-ol;
2-[8-fluoro-3-(2-fluoro-3'-isopropylbiphenyl-5-yl)imidazo[1,2-α]pyridin-7-yl]propan-2-ol;
2-[8-fluoro-3-(2,3',4'-trifluorobiphenyl-5-yl)imidazo[1,2-α]pyridin-7-yl]-propan-2-ol;
2-{8-fluoro-3-[4-fluoro-3-(quinolin-5-yl)phenyl]imidazo[1,2-α]pyridin-7-yl}propan-2-ol;

2-[3-(3'-chloro-2,2'-difluorobiphenyl-5-yl)-8-fluoroimidazo[1,2-α]pyridin-7-yl]propan-2-ol;
2-[3-(5'-chloro-2,2'-difluorobiphenyl-5-yl)-8-fluoroimidazo[1,2-α]pyridin-7-yl]propan-2-ol;
4,2'-difluoro-5'-[8-fluoro-7-(1-hydroxy-1-methylethyl)imidazo[1,2-α]pyridin-3-yl]biphenyl-3-carbonitrile;
2-{8-fluoro-3-[4-fluoro-3-(fur-2-yl)phenyl]imidazo[1,2-α]pyridin-7-yl}-propan-2-ol;
2-{3-[3-(benzo[1,3]dioxol-5-yl)-4-fluorophenyl]-8-fluoroimidazo[1,2-α]pyridin-7-yl}propan-2-ol;
2-[8-fluoro-3-(2-fluoro-3'-trifluoromethylbiphenyl-5-yl)imidazo[1,2-α]pyridin-7-yl]propan-2-ol;
2-{8-fluoro-3-[4-fluoro-3-(1H-pyrrol-2-yl)phenyl]imidazo[1,2-α]pyridin-7-yl}-propan-2-ol;
2-{3-[3-(benzofur-2-yl)-4-fluorophenyl]-8-fluoroimidazo[1,2-α]pyridin-7-yl}propan-2-ol;
2-[3-(2,2'-difluoro-4'-methoxybiphenyl-5-yl)-8-fluoroimidazo[1,2-α]pyridin-7-yl]propan-2-ol;
2-[8-fluoro-3-(2-fluoro-2'-methoxybiphenyl-5-yl)imidazo[1,2-α]pyridin-7-yl]propan-2-ol;
4,2'-difluoro-5'-(8-fluoro-7-trifluoromethylimidazo[1,2-α]pyridin-3-yl)-biphenyl-2-carbonitrile;
6,2'-difluoro-5'-(8-fluoro-7-trifluoromethylimidazo[1,2-α]pyridin-3-yl)-biphenyl-2-carbonitrile;
3-[3-(3,5-difluoropyridin-2-yl)-4-fluorophenyl]-8-fluoro-7-trifluoromethyl-imidazo[1,2-α]pyridine;
2-[2-fluoro-5-(8-fluoro-7-trifluoromethylimidazo[1,2-α]pyridin-3-yl)-phenyl]nicotinonitrile;
1-[2-fluoro-5-(8-fluoro-7-trifluoromethylimidazo[1,2-α]pyridin-3-yl)-phenyl]pyrrolidin-2-one;
3-(2,4'-difluoro-2'-methanesulfonylbiphenyl-5-yl)-8-fluoro-7-trifluoromethylimidazo[1,2-α]pyridine;
2-{8-fluoro-3-[4-fluoro-3-(2-methyl-2H-[1,2,4]triazol-3-ylmethoxy)phenyl]-imidazo[1,2-α]pyridin-7-yl}propan-2-ol;
8-fluoro-3-[4-fluoro-3-(1-methyl-1H-[1,2,3]triazol-4-ylmethoxy)phenyl]-7-trifluoromethylimidazo[1,2-α]pyridine;
or a pharmaceutically acceptable salt thereof.

8. A pharmaceutical composition which comprises a thereapeutically effective amount of a compound of claim 1 or a pharmaceutically acceptable salt thereof and a pharmaceutically acceptable carrier.

* * * * *